(12) United States Patent
Djupesland

(10) Patent No.: US 8,522,778 B2
(45) Date of Patent: *Sep. 3, 2013

(54) NASAL DEVICES

(75) Inventor: Per Gisle Djupesland, Oslo (NO)

(73) Assignee: OptiNose AS, Oslo (NO)

( * ) Notice: Subject to any disclaimer, the term of this patent is extended or adjusted under 35 U.S.C. 154(b) by 74 days.

This patent is subject to a terminal disclaimer.

(21) Appl. No.: 12/757,626

(22) Filed: Apr. 9, 2010

(65) Prior Publication Data

US 2011/0088691 A1    Apr. 21, 2011

Related U.S. Application Data

(63) Continuation of application No. 10/469,103, filed on Feb. 6, 2004, now Pat. No. 7,740,014.

(30) Foreign Application Priority Data

Feb. 26, 2001  (GB) .................................. 0104692.9
Feb. 26, 2002  (WO) .................. PCT/IB2002/001546

(51) Int. Cl.
 *A61M 15/00*    (2006.01)
 *A61M 16/00*    (2006.01)
 *A61M 15/08*    (2006.01)

(52) U.S. Cl.
 USPC ................................ 128/203.18; 128/203.15

(58) Field of Classification Search
 USPC ............. 128/200.14, 200.23, 203.12, 203.15, 128/203.18, 203.22, 207.18, 204.12, 206.11
 See application file for complete search history.

(56) References Cited

U.S. PATENT DOCUMENTS

| | | |
|---|---|---|
| 2,191,016 A | 2/1940 | Hoffman |
| 2,434,875 A | 1/1948 | Turnbull et al. |
| 2,470,297 A | 5/1949 | Fields |
| 3,605,738 A | 9/1971 | Ciranna |
| 4,300,545 A | 11/1981 | Goodnow et al. |
| 4,801,093 A | 1/1989 | Brunet et al. |
| 5,269,296 A | 12/1993 | Landis |
| 5,322,057 A | 6/1994 | Raabe et al. |
| 5,477,852 A | 12/1995 | Landis et al. |
| 5,533,506 A | 7/1996 | Wood |
| 5,715,810 A | 2/1998 | Armstrong et al. |
| 5,727,546 A | 3/1998 | Clarke et al. |
| 5,813,397 A | 9/1998 | Goodman et al. |
| 6,029,662 A | 2/2000 | Marcon |

(Continued)

FOREIGN PATENT DOCUMENTS

CA    2319026    8/1999
DE    197 08 406    9/1998

(Continued)

OTHER PUBLICATIONS

U.S. Appl. No. 12/955,546, Djupesland.

(Continued)

*Primary Examiner* — Kristen Matter

(74) *Attorney, Agent, or Firm* — Lihua Zheng; Mary S. Consalvi; Proskauer Rose LLP

(57) ABSTRACT

A nasal delivery device for and a method of delivering a substance to a nasal cavity of a subject, the delivery device including: a nosepiece for fitting to a nostril of a subject; a substance supply unit for supplying a substance for delivery through the nosepiece; and a delivery prevention mechanism for preventing delivery of a substance through the nosepiece until the nosepiece is properly fitted to the nostril of the subject.

7 Claims, 19 Drawing Sheets

(56) References Cited

U.S. PATENT DOCUMENTS

| | | | |
|---|---|---|---|
| 6,119,694 | A | 9/2000 | Correa et al. |
| 6,379,312 | B2 | 4/2002 | O'Toole |
| 6,431,172 | B1 | 8/2002 | Bordewick |
| 6,461,322 | B1 | 10/2002 | Ritsche |
| 6,715,485 | B1 | 4/2004 | Djupesland |
| 7,322,355 | B2 | 1/2008 | Jones et al. |
| 7,347,201 | B2 | 3/2008 | Djupesland |
| 7,377,901 | B2 | 5/2008 | Djupesland et al. |
| 7,481,218 | B2 | 1/2009 | Djupesland |
| 7,543,581 | B2 | 6/2009 | Djupesland |
| 7,740,014 | B2 | 6/2010 | Djupesland |
| 7,784,460 | B2 | 8/2010 | Djupesland et al. |
| 7,841,337 | B2 | 11/2010 | Djupesland |
| 7,854,227 | B2 | 12/2010 | Djupesland |
| 7,934,503 | B2 | 5/2011 | Djupesland |
| 7,975,690 | B2 | 7/2011 | Djupesland |
| 8,047,202 | B2 | 11/2011 | Djupesland |
| 2003/0005926 | A1 | 1/2003 | Jones et al. |
| 2004/0112379 | A1 | 6/2004 | Djupesland |
| 2004/0182388 | A1 | 9/2004 | Djupesland |
| 2005/0235992 | A1 | 10/2005 | Djupesland |
| 2006/0219240 | A1 | 10/2006 | Djupesland |
| 2006/0219241 | A1 | 10/2006 | Djupesland |
| 2006/0225732 | A1 | 10/2006 | Djupesland |
| 2006/0231094 | A1 | 10/2006 | Djupesland |
| 2007/0039614 | A1 | 2/2007 | Djupesland |
| 2007/0125371 | A1 | 6/2007 | Djupesland |
| 2008/0161771 | A1 | 7/2008 | Djupesland |
| 2008/0163874 | A1 | 7/2008 | Djupesland |
| 2008/0221471 | A1 | 9/2008 | Djupesland |
| 2008/0223363 | A1 | 9/2008 | Djupesland |
| 2008/0289629 | A1 | 11/2008 | Djupesland |
| 2009/0293873 | A1 | 12/2009 | Djupesland |
| 2009/0304802 | A1 | 12/2009 | Djupesland |
| 2009/0314293 | A1 | 12/2009 | Djupesland |
| 2009/0320832 | A1 | 12/2009 | Djupestand |
| 2010/0035805 | A1 | 2/2010 | Hafner |
| 2010/0051022 | A1 | 3/2010 | Djupesland |
| 2010/0057047 | A1 | 3/2010 | Djupesland |
| 2010/0242959 | A1 | 9/2010 | Djupesland |
| 2010/0282246 | A1 | 11/2010 | Djupesland |
| 2010/0288275 | A1 | 11/2010 | Djupesland |
| 2010/0300439 | A1 | 12/2010 | Djupesland |
| 2011/0023869 | A1 | 2/2011 | Djupesland |
| 2011/0053827 | A1 | 3/2011 | Hafner |
| 2011/0088690 | A1 | 4/2011 | Djupesland |
| 2011/0114087 | A1 | 5/2011 | Djupesland |
| 2011/0126830 | A1 | 6/2011 | Djupesland |
| 2011/0259329 | A1 | 10/2011 | Djupesland |

FOREIGN PATENT DOCUMENTS

| | | |
|---|---|---|
| DE | 198 25 434 | 8/1999 |
| EP | 0 577 448 | 1/1994 |
| EP | 1 082 971 | 3/2001 |
| GB | 2 316 451 | 2/1998 |
| GB | 2 349 092 | 10/2000 |
| JP | 11033117 | 2/1999 |
| WO | 92/21404 | 12/1992 |
| WO | 98/53869 | 12/1998 |
| WO | 00/51672 | 9/2000 |
| WO | 02/00281 | 1/2002 |

OTHER PUBLICATIONS

U.S. Appl. No. 12/973,317, Djupesland.
U.S. Appl. No. 13/063,963, Djupesland.
U.S. Appl. No. 13/099,183, Djupesland.
U.S. Appl. No. 13/180,492, Djupesland.
U.S. Appl. No. 13/244,499, Djupesland.
International Search Report for International Application No. PCT/IB2009/007108, Date of Mailing Jun. 6, 2011 (3 pages).
International Search Report for International Application No. PCT/IB2009/001546, Date of Mailing Apr. 12, 2002 (3 pages).

NASAL DEVICES

CROSS REFERENCE TO RELATED APPLICATIONS

This application is a continuation of U.S. Ser. No. 10/469,103 filed Feb. 6, 2004, which issued as U.S. Pat. No. 7,740,014 on Jun. 22, 2010, and which is a US National Phase of International Application No. PCT/IB02/01546 filed Feb. 26, 2002 and published in the English language. This application claims foreign priority to GB 0104692.9 filed Feb. 26, 2001.

The present invention relates to a nasal delivery device for and a method of delivering a substance, in particular one of a liquid, as a suspension or solution, or a powder containing a medicament, especially systemic or topical pharmaceuticals, to the nasal airway of a subject.

BACKGROUND OF THE INVENTION

Referring to FIG. 1, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitionin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as *helicobacter pylori* infections which cause gastric ulcers.

WO-A-00/51672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

SUMMARY OF THE INVENTION

It is an aim of the present invention to provide improved nasal delivery devices and nasal delivery methods for providing for the improved delivery of a substance to a nasal cavity of subject, in particular nasal delivery devices and nasal delivery methods which allow for actuation thereof only when fitted correctly to a nostril of a subject.

In particular, the present applicant has recognized that actuation of a nasal delivery device at a predetermined pressure provides for self-regulation of the flow rate of the flow delivered through the nasal airway, and also allows for actuation even in the event of complete obstruction of the nasal airway.

The flow rate through the nasal airway is determined by the actual nasal patency or resistance, and thus, for an open nasal airway, that is, a nasal airway having a low flow resistance, the flow rate is desirably low for a given actuation pressure, and for a congested nasal airway, that is, a nasal airway having a high flow resistance, the flow rate is desirably high for the same given actuation pressure. Regulation of the delivered flow occurs completely automatically. A particular advantage of using pressure as the triggering parameter, as opposed to flow alone, is that substance can be delivered to a nasal passageway even in the rare event of complete nasal obstruction. The internal dimensions/shape, and hence flow resistance, of the nosepiece ensure that substance is released at a maximum flow as determined by the internal geometry. At this flow, the driving pressure will reach the predetermined actuation pressure. Pressure triggering is for most purposes sufficient, but, in a preferred embodiment can be integrated with flow-triggering.

In one aspect the present invention provides a nasal delivery device for delivering a substance to a nasal cavity of a subject, including: a nosepiece for fitting to a nostril of a subject; a substance supply unit for supplying a substance for delivery through the nosepiece; and a delivery prevention mechanism for preventing delivery of a substance through the nosepiece until the nosepiece is properly fitted to the nostril of the subject.

In one embodiment the delivery device further includes: first and second members movable relative to one another between first and second configurations, and a biasing element for normally biasing the first and second members to one of the first and second configurations, whereby a predeterminable biasing force provided by the biasing element has to be overcome in properly fitting the nosepiece to the nostril of the subject.

Preferably, the delivery device further includes: a flow path fluidly connected to the nosepiece through which a gas flow is delivered to the nosepiece.

In one embodiment the delivery prevention mechanism comprises a blocking element which is movable to block the flow path, and thereby prevent the delivery of the gas flow to the nosepiece, until the nosepiece is properly fitted to the nostril of the subject.

Preferably, the delivery device further includes: first and second members movable relative to one another between first and second configurations, one of the members defining at least a part of the flow path, and the other member including the blocking element and blocking the flow path in one of the first and second configurations.

More preferably, the delivery device further includes: a biasing element for normally biasing the first and second members to the one of the first and second configurations, whereby a predeterminable biasing force provided by the biasing element has to be overcome in properly fitting the nosepiece to the nostril of the subject.

In another embodiment the delivery prevention mechanism comprises a vent which is openable to vent the gas flow from the flow path, and thereby prevent the delivery of the gas flow to the nosepiece, until the nosepiece is properly fitted to the nostril of the subject.

Preferably, the delivery device further includes: first and second members movable relative to one another between first and second configurations, one of the members defining at least a part of the flow path and defining at least in part the vent, and the other member being configured such that the vent is open in one of the first and second configurations and closed in the other of the first and second configurations.

More preferably, the delivery device further includes: a biasing element for normally biasing the first and second members to the one of the first and second configurations, whereby a predeterminable biasing force provided by the biasing element has to be overcome in properly fitting the nosepiece to the nostril of the subject.

Preferably, the other member comprises the nosepiece.

In a further embodiment the delivery prevention mechanism is provided by the nosepiece which includes at least one aperture in the outer surface thereof, the at least one aperture being fluidly connected to the flow path and located such as to be closed by the nostril when the nosepiece is properly inserted in the nostril of the subject, the substance supply unit being inoperable when the at least one aperture is open to atmosphere and operable when the at least one aperture is closed by the nostril of the subject.

Preferably, the nosepiece includes a plurality of apertures disposed about the outer periphery thereof.

In a yet further embodiment the delivery prevention mechanism is provided by the nosepiece which comprises an outer member for engagement with a nostril of the subject, at least a part of which outer member is flexible, and an inner member configured such as to support the at least flexible part of the outer member when the nosepiece is properly inserted in a nostril of the subject.

Preferably, the at least part flexible member is a resilient member.

More preferably, the outer member is a flexible tubular member.

Preferably, the inner member comprises a tubular member.

In a still further embodiment the delivery prevention mechanism is provided by the nosepiece which is expandable on generation of a pressure in the flow path to seal with a nostril of the subject.

Preferably, the nosepiece includes an outer surface for engagement with a nostril of the subject, at least a part of which is flexible, and an inner surface in fluid communication with the flow path, at least a part of which is flexible, such that application of a pressure to the inner surface causes deflection of the outer surface such as to sealingly engage the nostril of the subject.

In a still yet further embodiment the delivery prevention mechanism is configured to prevent delivery of a substance through the nosepiece until a predeterminable application force has been applied to the delivery device in fitting the nosepiece to a nostril of the subject.

Preferably, the delivery device further includes: a biasing element for transferring the application force to the nosepiece.

In one embodiment the delivery device further includes: a mouthpiece through which the subject in use exhales; and wherein the flow path fluidly connects the nosepiece and the mouthpiece, whereby exhaled air from an exhalation breath is delivered through the flow path.

In another embodiment the delivery device further includes: a gas supply unit for supplying a gas flow; and wherein the flow path fluidly connects the nosepiece and the gas supply unit, whereby a gas flow from the gas supply unit is delivered through the flow path.

Preferably, the delivery device further includes: a mouthpiece through which the subject in use exhales; and wherein the gas supply unit is an exhalation breath-actuated unit and fluidly connected to the mouthpiece such as to be actuated on exhalation by the subject through the same.

Preferably, the substance supply unit is actuatable to supply a substance, and the delivery prevention mechanism comprises an actuation prevention mechanism for preventing actuation of the substance supply unit until the nosepiece is properly fitted to the nostril of the subject.

More preferably, the delivery device further includes: an exhalation breath-actuated trigger mechanism for actuating the substance supply unit.

In one embodiment the trigger mechanism is configured such as to prevent actuation thereof until a predeterminable application force has been applied to the delivery device in fitting the nosepiece to a nostril of the subject.

Preferably, the delivery device further includes: a biasing element for transferring the application force to the nosepiece.

In one embodiment the trigger mechanism is configured to actuate the substance supply unit at a predeterminable pressure.

In another embodiment the trigger mechanism is configured to actuate the substance supply unit at a predeterminable flow rate.

In a further embodiment the trigger mechanism is configured to actuate the substance supply unit at one or both of a predeterminable pressure and a predeterminable flow rate.

Preferably, the substance supply unit includes a dosing unit for supplying at least one substance.

In one embodiment the dosing unit comprises a nebulizer for supplying an aerosol.

In another embodiment the dosing unit comprises an aerosol canister for supplying an aerosol.

In a further embodiment the dosing unit comprises a delivery pump unit for supplying an aerosol.

In one preferred embodiment the dosing unit comprises a liquid pump unit for supplying a liquid aerosol.

In another preferred embodiment the dosing unit comprises a powder pump unit for supplying a powder aerosol.

In a yet further embodiment the dosing unit comprises a powder delivery unit for delivering a powder aerosol.

In another aspect the present invention provides a nasal delivery device for delivering a substance to a nasal cavity of a subject, including: a nosepiece for fitting to a nostril of a subject; and a substance supply unit for supplying a substance, the substance supply unit including a trigger mechanism for actuating the same at one or both of a predeterminable pressure and a predeterminable flow rate.

In one embodiment the trigger mechanism is configured to actuate the substance supply unit at a predeterminable pressure.

In another embodiment the trigger mechanism is configured to actuate the substance supply unit at a predeterminable flow rate.

In a further aspect the present invention provides a nasal delivery device for delivering a substance to a nasal cavity of a subject, including: a nosepiece for fitting to a nostril of a subject; and a flow path fluidly connected to the nosepiece; wherein the nosepiece is configured to expand on generation of a pressure in the flow path to seal with a nostril of the subject.

Preferably, the nosepiece includes an outer surface for engagement with a nostril of the subject, at least a part of which is flexible, and an inner surface in fluid communication with the flow path, at least a part of which is flexible, such that application of a pressure to the inner surface causes deflection of the outer surface such as to sealingly engage the nostril of the subject.

Preferably, the at least part of the outer surface of the nosepiece is a resilient element.

Preferably, the at least part of the inner surface of the nosepiece is a resilient element.

In a yet further aspect the present invention provides a nasal delivery device for delivering a substance to a nasal cavity of a subject, comprising: first and second body members relatively movable between a first, inoperative position and a second, operative position; a biasing element for biasing the body members to the inoperative position; a nosepiece provided to one of the body members for fitting to the nostril of a subject; a substance supply unit actuatable to supply substance; and an actuation prevention mechanism for preventing the actuation of the device when the body members are in the inoperative position.

In one embodiment one of the body members includes a mouthpiece through which a subject in use exhales to actuate the substance delivery unit and the other of the body members includes the nosepiece and a closure member which closes the mouthpiece when the body members are in the inoperative position, thereby preventing actuation of the substance supply unit.

More preferably, the mouthpiece includes a resilient section which is deflected by the closure member to close the mouthpiece when the body members are in the inoperative position.

In another embodiment one of the body members includes a mouthpiece through which a subject in use exhales to actuate the substance supply unit and the other of the body members includes at least one port, the at least one port being in communication with the mouthpiece when the body members are in the inoperative position such as to allow the exhaled air to flow therethrough and prevent the actuation of the substance supply unit.

In a still further aspect the present invention provides a breath-actuated nasal delivery device, comprising: a body member including a mouthpiece through which a subject in use exhales to actuate the device; a nosepiece for fitting to the nostril of the subject, the nosepiece being movably disposed to the body member between a first, inoperative position in which air exhaled through the mouthpiece is vented to atmosphere to prevent the actuation of the device and a second, operative position; and a biasing element for biasing the nosepiece to the inoperative position.

In a still yet further aspect the present invention provides a breath-actuated nasal delivery device, comprising: a body member including an air chamber and a mouthpiece in fluid communication therewith through which a subject in use exhales to actuate the device; and a nosepiece for fitting to a nostril of the subject, the nosepiece including at least one fluid channel extending from the outer surface of the nosepiece to the air chamber and being configured such as to be closed by the nostril when the nosepiece is properly inserted into the nostril of the subject, the device being inoperable when the at least one fluid channel is open to atmosphere and operable when the at least one fluid channel is closed by the nostril of the subject.

BRIEF DESCRIPTION OF THE DRAWINGS

Preferred embodiments of the present invention will now be described hereinbelow by way of example only with reference to the accompanying drawings, in which:

FIGS. 2(a) to (c) illustrate an exhalation breath-actuated nasal delivery device in accordance with a first embodiment of the present invention.

DETAILED DESCRIPTION OF THE INVENTION

Figure 1:
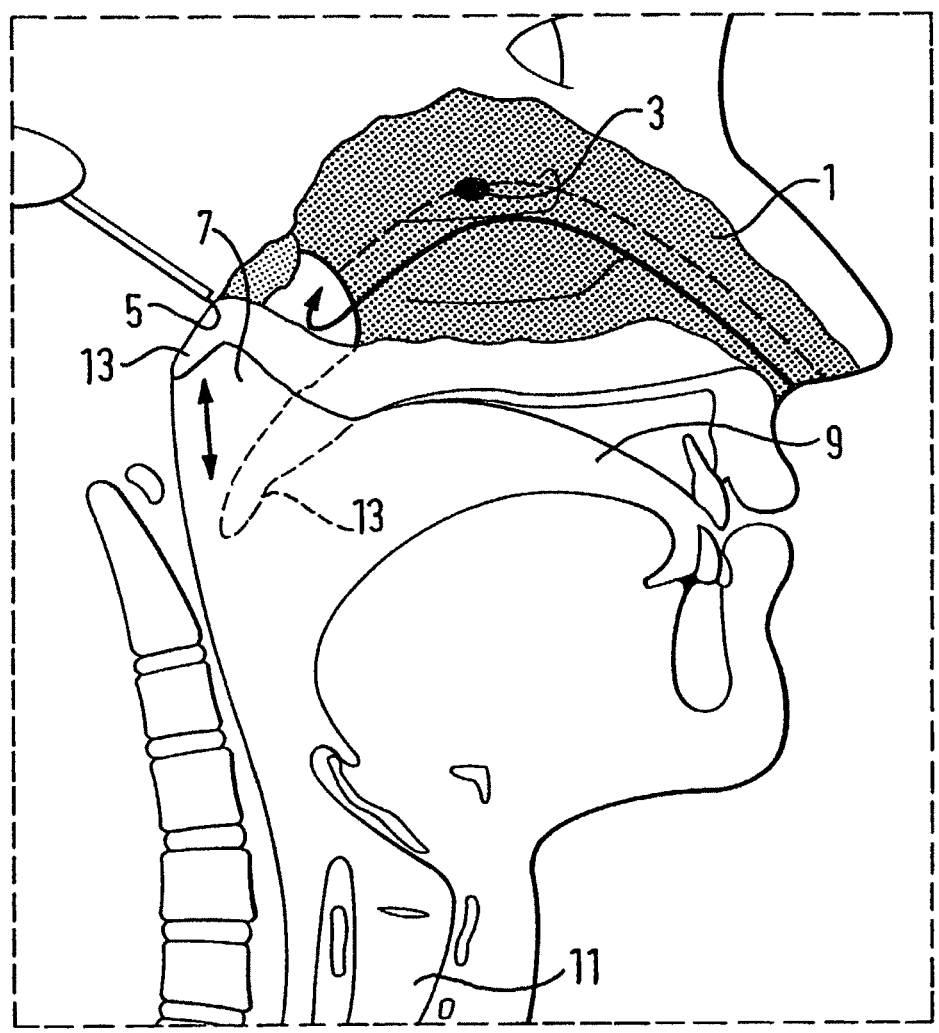
FIG. 1 diagrammatically illustrates the upper airway of a human subject.
Figure 2A:
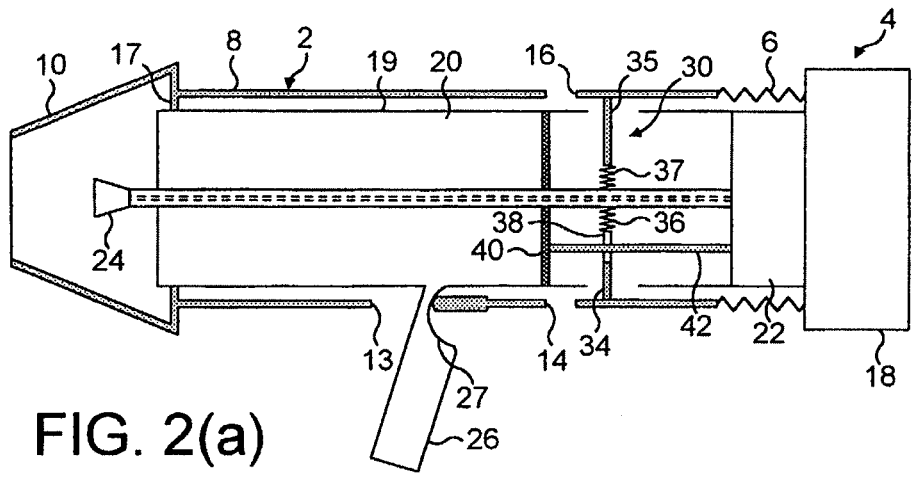
FIG. 2(a) schematically illustrates a nasal delivery device in accordance with a first embodiment of the present invention.
Figure 2B:
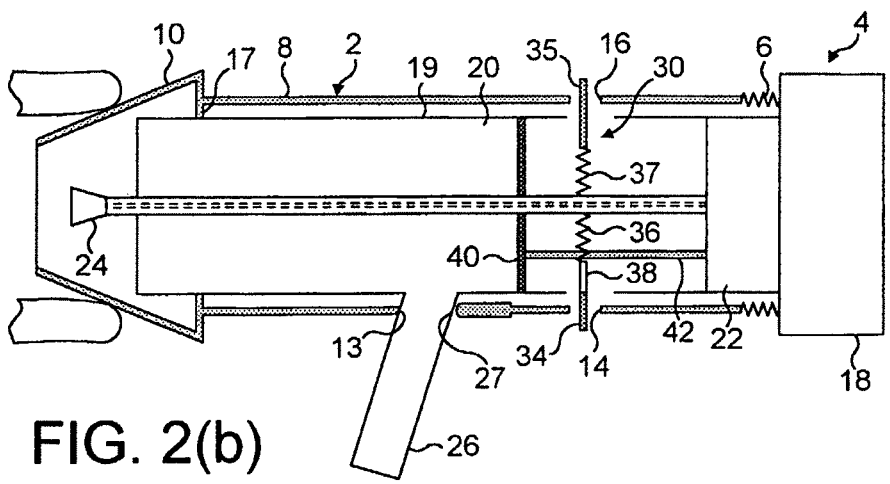
FIG. 2(b) schematically illustrates the nasal delivery device of FIG. 2(a) in an operative configuration.

The delivery device comprises a housing 2, a delivery unit 4 which is slideably disposed relative to the housing 2 between a first, inoperative position (as illustrated in FIG. 2(a)) in which the delivery device is inoperative and a second, operative position (as illustrated in FIG. 2(b)) in which the delivery device is actuatable to deliver substance, and a biasing element 6, in this embodiment a compression spring, for normally biasing the delivery unit 4 to the inoperative position.

The housing 2 comprises a tubular member 8, in this embodiment a cylindrical member, and a nosepiece 10 for fitting in one nostril of a subject which is disposed to one, the distal, end of the tubular member 8.

The tubular member 8 includes a clearance aperture 12 in the peripheral wall thereof which is configured to receive a mouthpiece 26 on the delivery unit 4, the function of which mouthpiece 26 will be described in more detail hereinbelow.

The tubular member 8 further includes first and second latching apertures 14, 16 in the peripheral wall thereof, in this embodiment diametrically opposed apertures, which are configured to receive respective ones of first and second latching members 34, 35 of a trigger mechanism 30 in the delivery unit 4, the function of which trigger mechanism 30 will be described in more detail hereinbelow.

The tubular member 8 further includes a sealing lip 17, in this embodiment an annular lip, which is disposed on the inner peripheral wall thereof, in this embodiment at one, the distal, end thereof, and acts to seal the housing 2 to the delivery unit 4.

The delivery unit 4 comprises a main body 18 which includes a tubular member 19, in this embodiment a cylindrical member, which is slideably disposed within the housing 2, with the outer peripheral wall at the one, distal end of the tubular member 19 being in sealing engagement with the sealing lip 17 at the inner peripheral wall of the tubular member 8 of the housing 2. The tubular member 19 of the main body 18 includes a cavity 20 at the one end thereof which is in fluid communication with the nosepiece 10 such that exhalation breath introduced thereinto is directed through the nosepiece 10.

The delivery unit 4 further comprises a substance supply unit 22 for delivering metered doses of a substance, in this embodiment an aerosol canister for delivering metered volumes of a propellant, preferably a hydrofluoroalkane (HFA) propellant or the like, containing medicament, either as a suspension or solution, and a nozzle 24 which is fluidly connected to the substance supply unit 22 for providing an aerosol spray through the nosepiece 10. In this embodiment the nozzle 24 is disposed in the nosepiece 10 co-axially with the same.

The substance supply unit 22 is pre-primeable, in this embodiment by loading a resilient element, and includes a release mechanism which, when triggered, releases the resilient element and actuates the substance supply unit 22 to deliver a metered dose of a substance.

In an alternative embodiment the substance supply unit 22 could comprise a mechanical delivery pump, in particular a liquid delivery pump or a powder delivery pump, which delivers metered doses of a substance on actuation thereof.

The delivery unit 4 further comprises a mouthpiece 26 which is in selective fluid communication with the cavity 20 in the main body 18 and through which a subject exhales to actuate the substance supply unit 22, as will be described in more detail hereinbelow.

The mouthpiece 26 includes a resilient section 27 which is movable between a first, closed position in which the mouthpiece 26 is substantially closed to prevent any significant exhalation therethrough and a second, open position in which the mouthpiece 26 is open and a subject can exhale therethrough, with the resilient section 27 being normally engaged by a part of the tubular member 8 of the housing 2 under the bias of the biasing element 6 to close the mouthpiece 26. With the delivery unit 4 in the inoperative position, the tubular member 8 of the housing 2 acts on the resilient section 27 of the mouthpiece 26 to close the same. With the delivery unit 4 in the operative position, the mouthpiece 26 is not engaged by the tubular member 8 of the housing 2 and is in fluid communication with the cavity 20, thereby allowing for actuation of the delivery device.

The delivery unit 4 further comprises a trigger mechanism 30 which is configured to prevent actuation of the substance supply unit 22 until the nosepiece 10 is correctly inserted in the nostril of a subject by biasing the delivery unit 4 to the operative position and cause actuation of the substance supply unit 22 on generation of a predetermined pressure within the cavity 20 in the main body 18.

In an alternative embodiment the trigger mechanism 30 could be configured to cause actuation of the substance supply unit 22 on generation of a predetermined flow rate through the mouthpiece 26.

The trigger mechanism 30 includes first and second latching members 34, 35 and first and second resilient elements 36, 37 which act to bias respective ones of the first and second latching members 34, 35 radially outwardly with respect to the delivery unit 4 to a latching position in which the first and second latching members 34, 35 are located in respective ones of the first and second latching apertures 14, 16 in the tubular member 8 of the housing 2. The first latching member 34 includes an aperture 38 therein to accommodate a link 42, as will be described in more detail hereinbelow. With the delivery unit 4 in the inoperative position, that is, not biased to the operative position, the latching members 34, 35 are not located in the respective ones of the latching apertures 14, 16, thereby providing an indication to a subject that the delivery device is not properly inserted. With the delivery unit 4 in the operative position, that is, biased sufficiently that the delivery device is properly inserted, the latching members 34, 35 are located in the respective ones of the latching apertures 14, 16, thereby providing an indication to a subject that the delivery device is properly inserted, and hence ready for actuation by exhaling through the mouthpiece 26. Following actuation of the substance supply unit 22, the latching members 34, 35 can be released from the respective ones of the latching apertures 14, 16, and hence the delivery unit 4 returned to the inoperative position, by depressing the latching members 34, 35; the delivery unit 4 being returned to the inoperative position by the action of the biasing element 6.

Figure 2C:
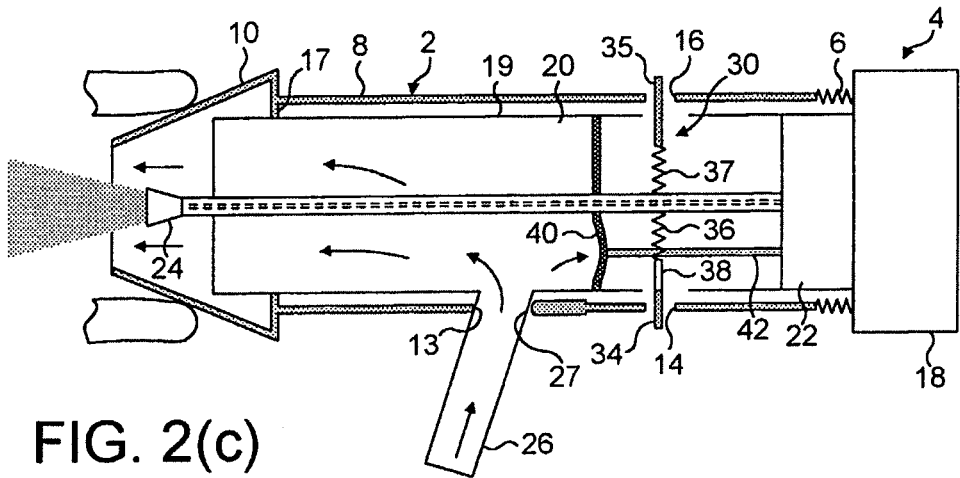
FIG. 2(c) schematically illustrates the nasal delivery device of FIG. 2(a) in an actuated configuration.

The trigger mechanism 30 further includes a flexible member 40, in this embodiment a resilient membrane, which defines a part of the wall of the cavity 20 in the main body 18, and a link 42 which extends through the aperture 38 in the first latching member 34 and couples the flexible member 40 and the release mechanism of the substance supply unit 22. The flexible member 40 is configured such as, on generation of a predetermined pressure within the cavity 20 in the main body 18, to be deflected sufficiently as to actuate the release mechanism of the substance supply unit 22 and deliver a metered dose of a substance (as illustrated in FIG. 2(*c*)).

With this configuration, the actuation of the delivery device is prevented until a proper sealing fit is achieved to the nostril of the subject. As will be understood, a sealing fit of the nosepiece 10 in the nostril of the subject is essential for the proper operation of the delivery device, as otherwise optimal delivery, in particular bi-directional flow through the nasal cavities, would not be achieved. Also, as the delivery device is inoperable until properly fitted, the patient learns intuitively to use the device properly. Moreover, the delivery device is operable even in the case of complete nasal obstruction, provided the nosepiece 10 is correctly positioned.

Figure 3A:
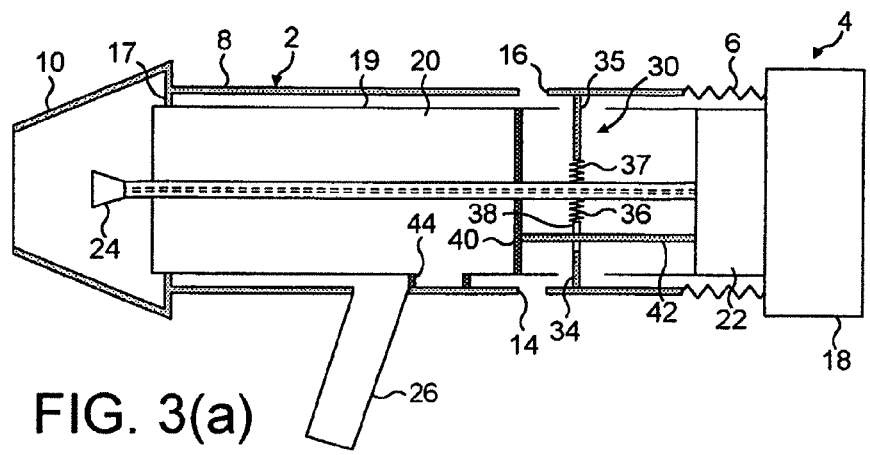
FIG. 3(a) schematically illustrates a nasal delivery device in accordance with a second embodiment of the present invention.
Figure 3B:
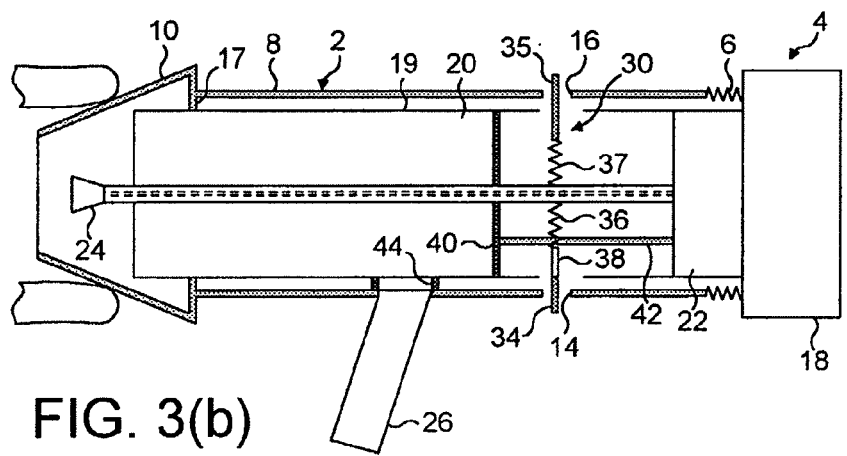
FIG. 3(b) schematically illustrates the nasal delivery device of FIG. 3(a) in an operative configuration.
Figure 3C:
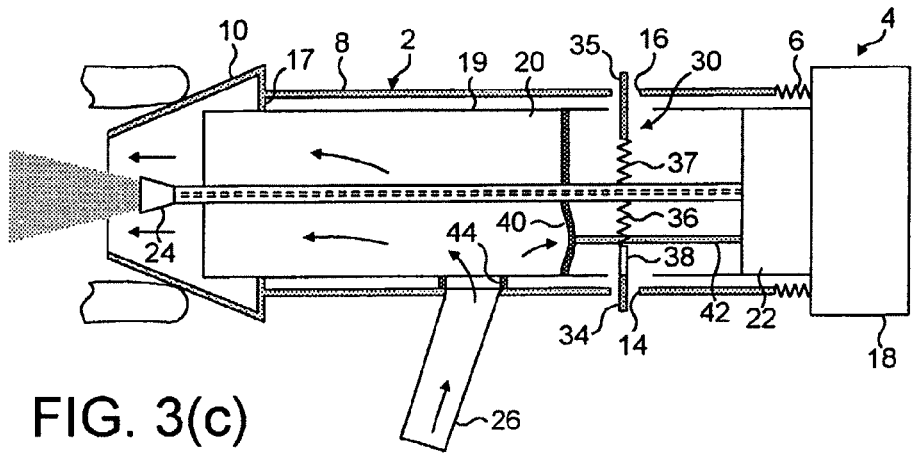
FIG. 3(c) schematically illustrates the nasal delivery device of FIG. 3(a) in an actuated configuration.

FIGS. 3(*a*) to (*c*) illustrate an exhalation breath-actuated nasal delivery device in accordance with a second embodiment of the present invention.

The nasal delivery device of this embodiment is very similar to the nasal delivery device of the above-described first embodiment, and thus, in order to avoid unnecessary duplication of description, only the differences will be described in detail, with like reference signs designating like parts The nasal delivery device of this embodiment differs from that of the above-described first embodiment only in that the housing 2 includes the mouthpiece 26, the mouthpiece 26 being of solid section and including no resilient section 27, and, in place of the mouthpiece 26, the tubular member 19 of the main body 18 includes an aperture 44 which is in sealing engagement with the inner peripheral wall of the tubular member 8 of the housing 2, with the aperture 44 being located such as to be out of fluid communication with the mouthpiece 26 when the delivery unit 4 is in the inoperative position (as illustrated in FIG. 3(a)) and in fluid communication with the mouthpiece 26 when the delivery unit 4 is in the operative position (as illustrated in FIG. 3(b)).

Operation of the delivery device is the same as for the delivery device of the above-described first embodiment, with the subject being unable to exhale through the mouthpiece 26 until the mouthpiece 26 is in registration with the aperture 44 in the tubular member 19 of the main body 18. In a preferred embodiment the aperture 44 is shaped and/or sized such that the delivery unit 4 has to be biased to the operative position before a sufficient pressure can be generated in the cavity 20 in the main body 18 as to deflect the flexible member 40 of the trigger mechanism 30 and cause actuation of the same.

In an alternative embodiment, where the aperture 44 is configured such as to provide for actuation of the triggering mechanism 30 only when the delivery unit 4 is biased to the operative position, the latching members 34, 35 and the associated biasing elements 36, 37 could be omitted as a user would experience significant flow resistance on attempting to exhale through the mouthpiece 26 until the delivery unit 4 was biased to the operative position.

Figure 4A:
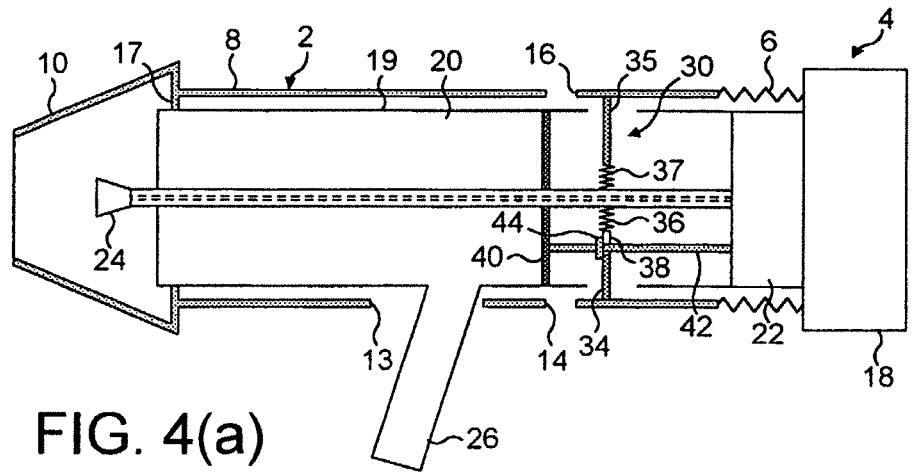
FIG. 4(a) schematically illustrates a nasal delivery device in accordance with a third embodiment of the present invention.
Figure 4B:
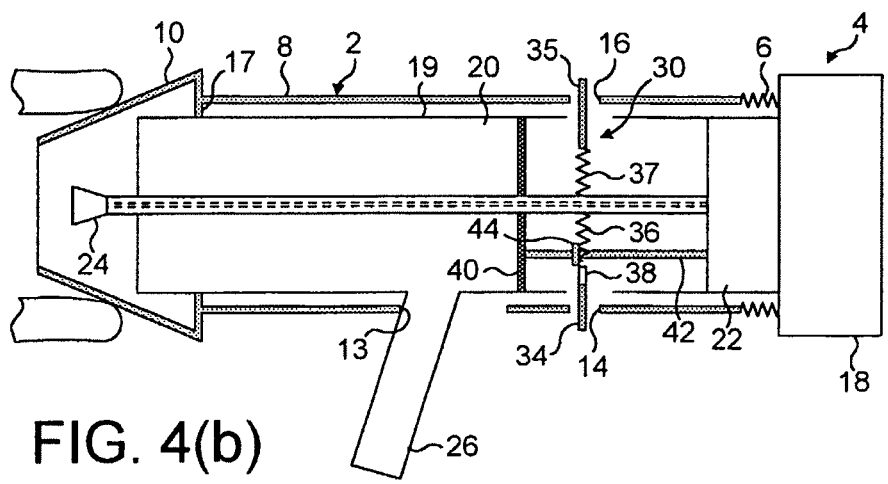
FIG. 4(b) schematically illustrates the nasal delivery device of FIG. 4(a) in an operative configuration.
Figure 4C:
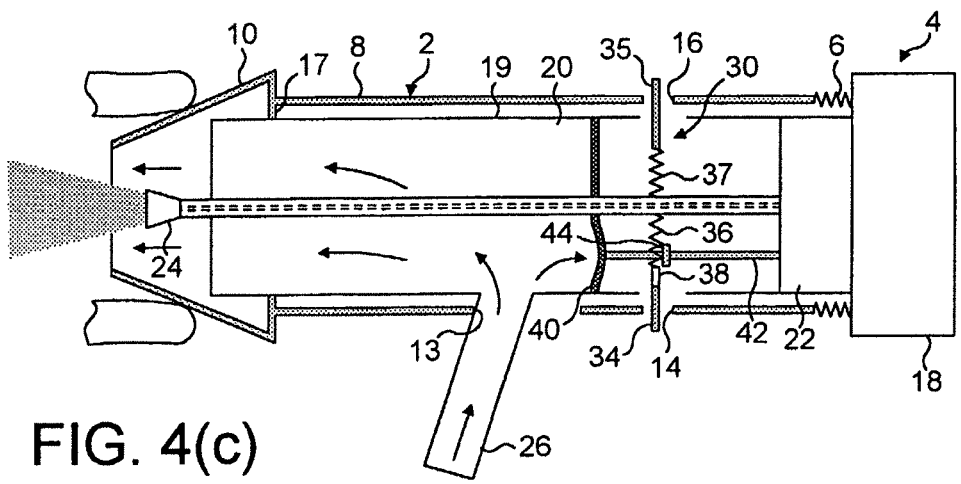
FIG. 4(c) schematically illustrates the nasal delivery device of FIG. 4(a) in an actuated configuration.

FIGS. 4(a) to (c) illustrate an exhalation breath-actuated nasal delivery device in accordance with a third embodiment of the present invention.

The nasal delivery device of this embodiment is very similar to the nasal delivery device of the above-described first embodiment, and thus, in order to avoid unnecessary duplication of description, only the differences will be described in detail, with like reference signs designating like parts.

The nasal delivery device of this embodiment differs from that of the above-described first embodiment only in that the mouthpiece 26 is of solid section and in permanent fluid communication with the cavity 20 in the main body 18, and in having a modified trigger mechanism 30 which prevents movement of the link 42 while the latching members 34, 35 are not in the latching position.

In this embodiment the link 42 includes a flange 44 which is of greater dimension than the aperture 38 in the first latching member 34, which flange 44 acts to prevent movement of the link 42, and hence actuation of the release mechanism of the substance supply unit 22, while the latching members 34, 35 are in other than the latching position.

With the delivery unit 4 in the inoperative position, that is, not biased to the operative position, the latching members 34, 35 are maintained in a locking position by engagement with the inner peripheral wall of the tubular member 8 of the housing 2. With the delivery unit 4 in the operative position, that is, biased to the operative position, the first latching member 34 is located radially outwardly of the link 42 such that movement of the link 42 is not prevented by engagement of the flange 44 on the link 42 and the first latching member 34, and hence the link 42 is free to be move and actuate the release mechanism of the substance supply unit 22.

Operation of the delivery device is the same as for the delivery device of the above-described first embodiment, with a subject being able to exhale through the mouthpiece 26, but the trigger mechanism 30 not being operable, and hence the substance supply unit 22 not being actuatable, until the delivery unit 4 is properly biased to the operative position.

Figure 5A:
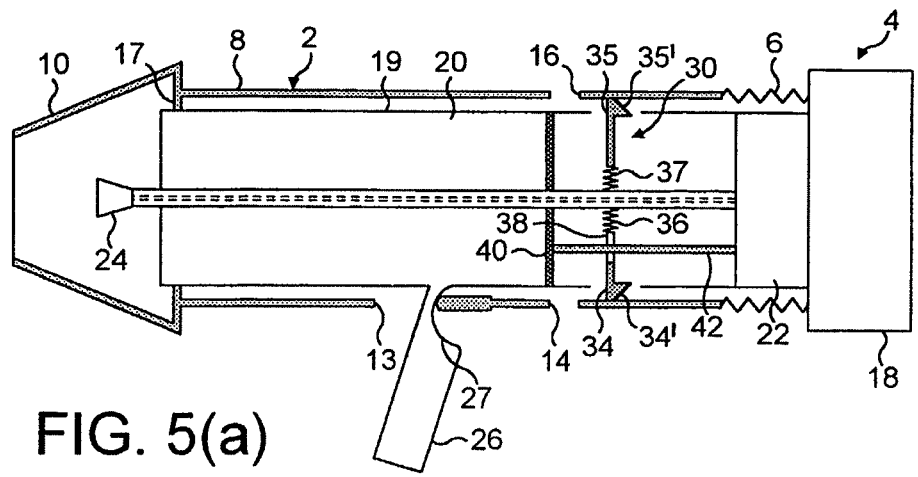
FIG. 5(a) schematically illustrates a nasal delivery device in accordance with a fourth embodiment of the present invention.
Figure 5B:
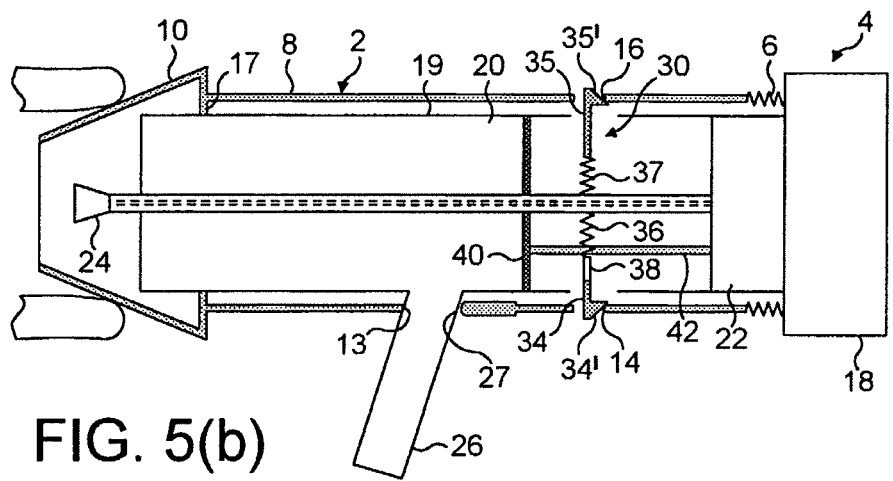
FIG. 5(b) schematically illustrates the nasal delivery device of FIG. 5(a) in an operative configuration.
Figure 5C:
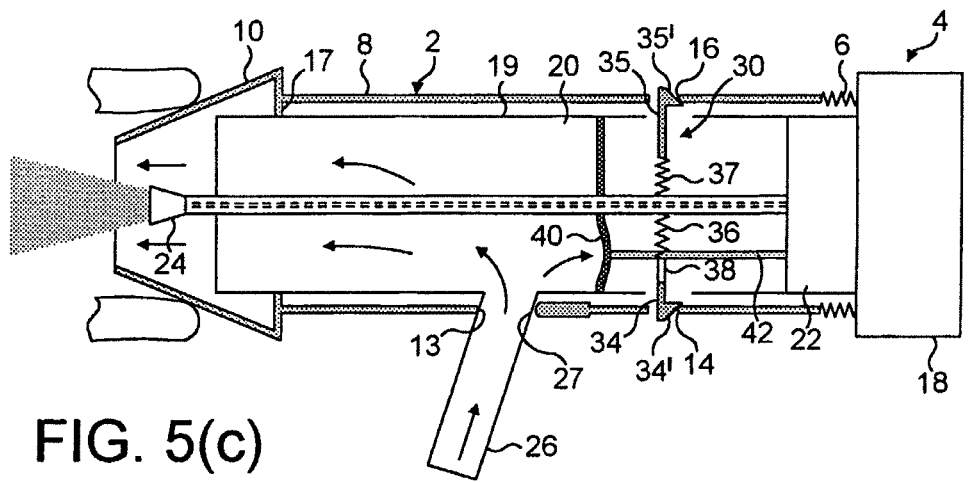
FIG. 5(c) schematically illustrates the nasal delivery device of FIG. 5(a) in an actuated configuration.

FIGS. 5(a) to (c) illustrate an exhalation breath-actuated nasal delivery device in accordance with a fourth embodiment of the present invention.

The nasal delivery device of this embodiment is very similar to the nasal delivery device of the above-described first embodiment, and thus, in order to avoid unnecessary duplication of description, only the differences will be described in detail, with like reference signs designating like parts.

The nasal delivery device of this embodiment differs from that of the above-described first embodiment only in that the first and second latching members 34, 35 include chamfered trailing edges 34', 35'. With this configuration, the latching members 34, 35 are automatically disengaged from the respective latching apertures 14, 16 under the action of the biasing element 6 when a biasing force is not applied to the delivery unit 4. In this way, a subject is required continuously required to apply a biasing force to the delivery unit 4 to maintain the delivery unit 4 in the operative position, thereby ensuring proper insertion of the nosepiece 10 throughout the delivery regime. It will be understood that the above-described second and third embodiments could be similarly modified.

Operation of the delivery device is the same as for the delivery device of the above-described first embodiment, except that a subject is required to bias the delivery unit 4 continuously to the operative position during the delivery regime.

Figure 6A:
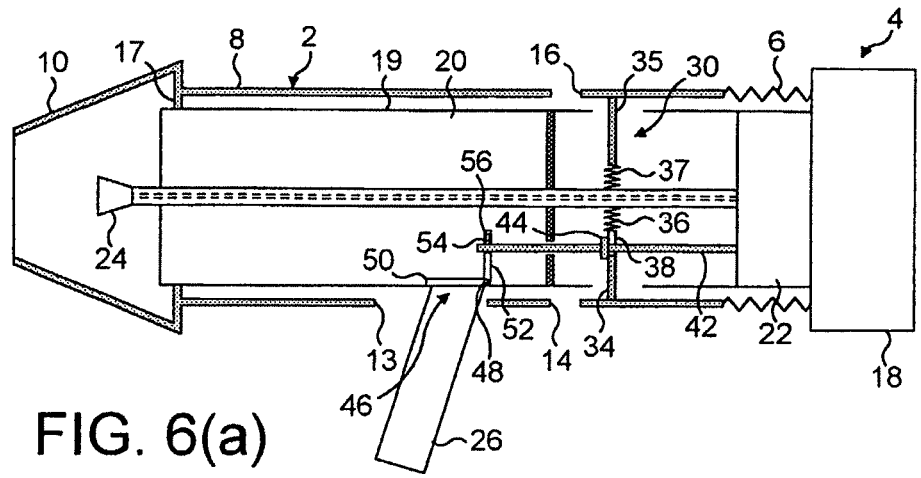
FIG. 6(a) schematically illustrates a nasal delivery device in accordance with a fifth embodiment of the present invention.
Figure 6B:
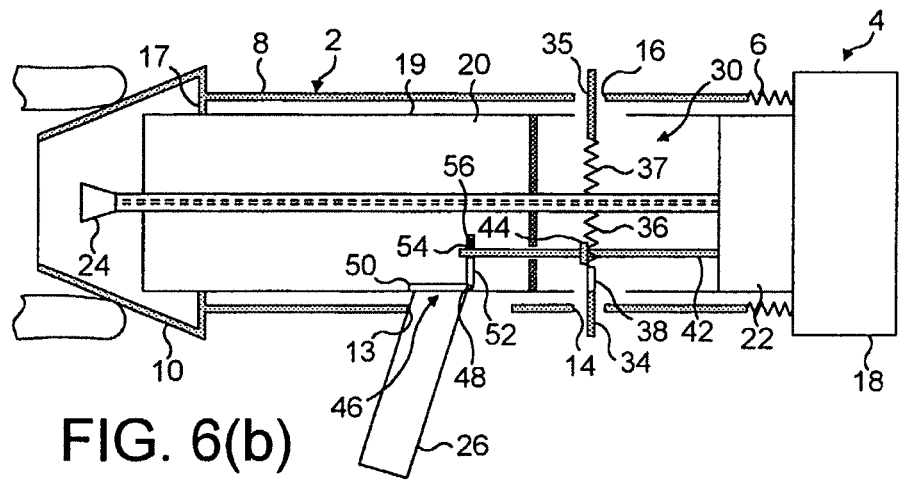
FIG. 6(b) schematically illustrates the nasal delivery device of FIG. 6(a) in an operative configuration.
Figure 6C:
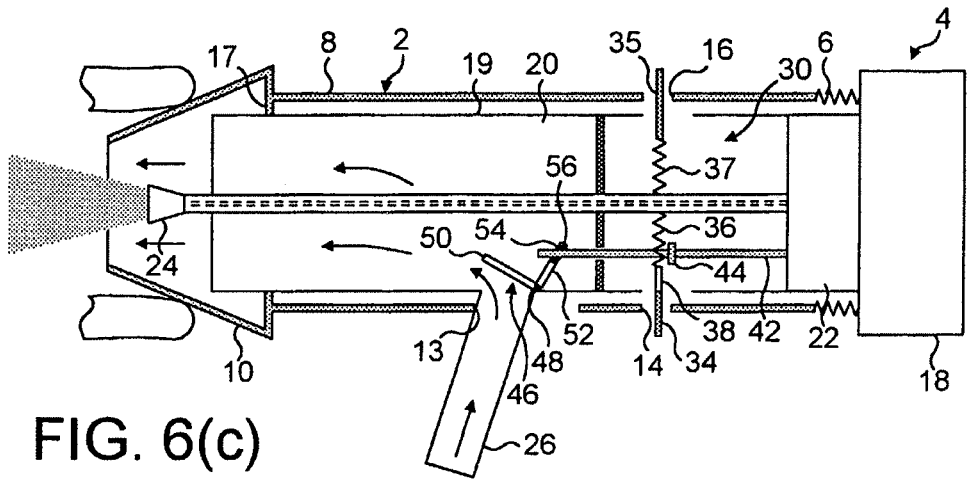
FIG. 6(c) schematically illustrates the nasal delivery device of FIG. 6(a) in an actuated configuration.

FIGS. 6(a) to (c) illustrate an exhalation breath-actuated nasal delivery device in accordance with a fifth embodiment of the present invention.

The nasal delivery device of this embodiment is very similar to the nasal delivery device of the above-described third embodiment, and thus, in order to avoid unnecessary duplication of description, only the differences will be described in detail, with like reference signs designating like parts.

The nasal delivery device of this embodiment differs from that of the above-described third embodiment only in that the trigger mechanism 40 includes a flap member 46 in place of the flexible membrane 40 for actuating the release mechanism of the substance supply unit 22 in response to the generation of a predetermined flow rate through the mouthpiece 26, and hence the cavity 20 in the main body 18 and the nosepiece 10. The flap member 46 is pivotally mounted about a pivot 48 to the main body 18 of the delivery unit 4. It will be understood that the above-described first, second, fourth and fifth embodiments could be similarly modified.

The flap member 46 comprises a vane 50 which is disposed at the outlet of the mouthpiece 26 such as to substantially close the same when in the non-actuated position and be acted upon by the exhalation breath of a user on exhalation through the mouthpiece 26. The flap member 46 further comprises an arm 52 which is coupled to the link 42. The link 42 includes a projection 54 and the arm 52 of the flap member 46 includes a slot 56 which captively receives the projection 54 on the link 42, whereby movement of the vane 50 of the flap member 46, which is possible only with the latching members 34, 35 in the latching position, acts to displace the link 42. With the latching members 34, 35 in other than the latching position, the trigger mechanism 30 is not actuatable. With this configuration, the vane 50 of the flap member 46 is rotated through a predetermined angle on generation of a predetermined flow rate through the mouthpiece 26, which rotation is translated to a predetermined displacement of the link 42, which displacement is such as to actuate the release mechanism of the substance supply unit 22.

Operation of the delivery device is the same as for the delivery device of the above-described third embodiment, with the delivery device being actuated by the generation of a predetermined flow rate as opposed to a predetermined pressure.

Figure 7A:
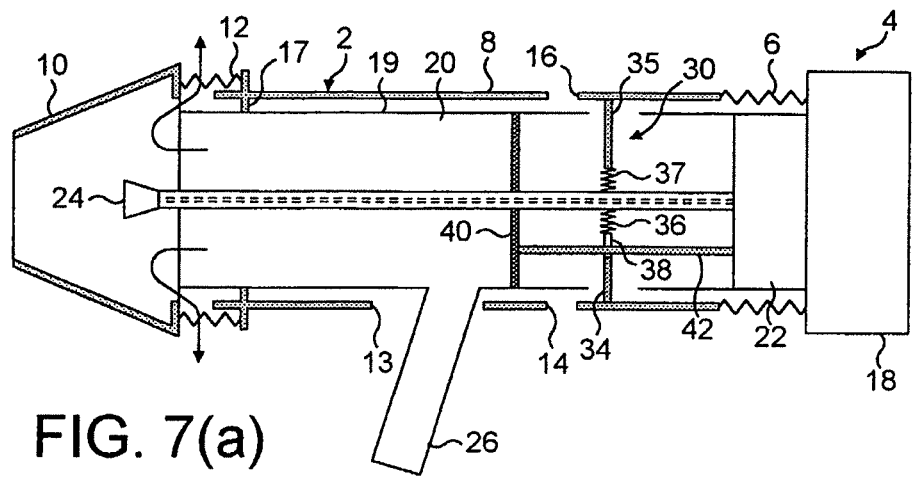
FIG. 7(a) schematically illustrates a nasal delivery device in accordance with a sixth embodiment of the present invention.
Figure 7B:
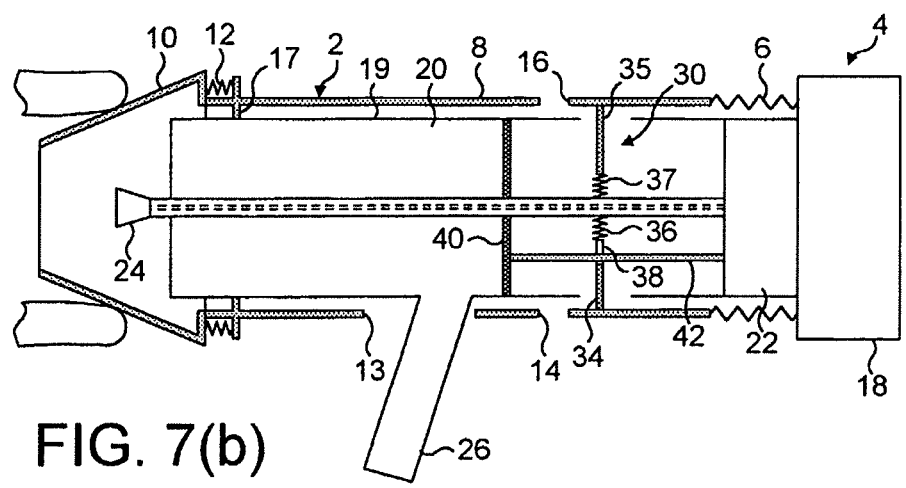
FIG. 7(b) schematically illustrates the nasal delivery device of FIG. 7(a) in an operative, but non-indicated configuration.
Figure 7C:
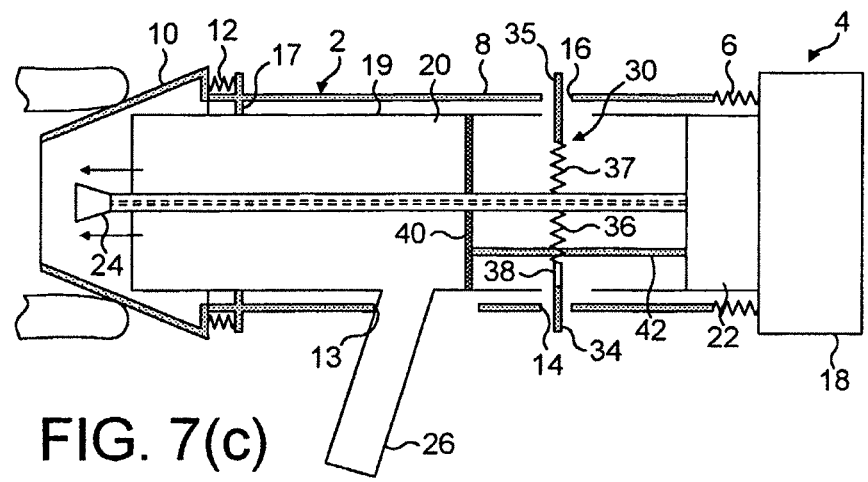
FIG. 7(c) schematically illustrates the nasal delivery device of FIG. 7(a) in an operative and indicated configuration.

FIGS. 7(a) to (c) illustrate an exhalation breath-actuated nasal delivery device in accordance with a sixth embodiment of the present invention.

The delivery device comprises a housing 2, a delivery unit 4 which is slideably disposed relative to the housing 2 between a first, rest position (as illustrated in FIGS. 7(a) and (b)) and a second, operative position (as illustrated in FIG. 7(c)) in which a user is provided with an indication that the delivery device is sufficiently inserted into a nostril of the user as to be actuatable to deliver substance, and a biasing element 6, in this embodiment a resilient element, particularly a compression spring, for normally biasing the delivery unit 4 to the rest position.

The housing 2 comprises a tubular member 8, in this embodiment a cylindrical member, a nosepiece 10 for fitting in a nostril of a user which is slideably disposed to one, the distal, end of the tubular member 8 between a first, open position (as illustrated in FIG. 7(a)) which is such as to define an aperture 11, in this embodiment an annular aperture, between the tubular member 8 and the nosepiece 10 and thereby provide a fluid communication path to the atmosphere, and a second, closed position (as illustrated in FIGS. 7(a) to (d)) in which the tubular member 8 and the nosepiece 10 are substantially in sealing engagement, and a biasing element 12, in this embodiment a resilient element, particularly a compression spring, for normally biasing the nosepiece 10 to the open position. In this embodiment the biasing element 12 has a biasing force which is such as to maintain the nosepiece 10 in the open position until a sufficient biasing force has been applied to the delivery unit 4 as for the nosepiece 10 to be sufficiently inserted in the nostril of a user.

The tubular member 8 includes a clearance aperture 13 in the peripheral wall thereof, which aperture 13 is configured to receive a mouthpiece 26 on the delivery unit 4, the function of which mouthpiece 26 will be described in more detail hereinbelow.

The tubular member 8 further includes first and second latching apertures 14, 16 in the peripheral wall thereof, in this embodiment diametrically opposed apertures, which are configured to receive respective ones of first and second latching members 34, 35 of a trigger mechanism 30 in the delivery unit 4, the function of which trigger mechanism 30 will be described in more detail hereinbelow.

The tubular member 8 further includes a sealing lip 17, in this embodiment an annular lip, which is disposed at the inner peripheral wall thereof, in this embodiment at one, the distal, end thereof, and acts to seal the housing 2 to the delivery unit 4.

The delivery unit 4 comprises a main body 18 which includes a tubular member 19, in this embodiment a cylindrical member, which is slideably disposed within the housing 2, with the outer peripheral wall at the one, distal end of the tubular member 19 being in sealing engagement with the sealing lip 17 at the inner peripheral wall of the tubular member 8 of the housing 2. The tubular member 19 of the main body 18 includes an air chamber 20 at the one end thereof which is in fluid communication with the nosepiece 10 such that exhalation breath introduced thereinto is directed through the nosepiece 10.

The delivery unit 4 further comprises a substance supply unit 22 for delivering metered doses of a substance, in this embodiment an aerosol canister for delivering metered volumes of a propellant, preferably a hydrofluoroalkane (HFA) propellant or the like, containing medicament, either as a suspension or solution.

In this embodiment the substance supply unit 22 is a primeable unit which is primed by loading a resilient element, particularly a compression spring, and includes a release mechanism which, when triggered, releases the resilient element and actuates the substance supply unit 22 to deliver a metered dose of a substance.

In an alternative embodiment the substance supply unit 22 could comprise a mechanical delivery pump, in particular a liquid delivery pump or a powder delivery pump, which delivers metered doses of a substance on actuation thereof.

The delivery unit 4 further comprises a nozzle 24 which is fluidly connected to the substance supply unit 22 for providing an aerosol spray through the nosepiece 10. In this embodiment the nozzle 24 is disposed in the nosepiece 10 co-axially with the same.

The delivery unit 4 further comprises a mouthpiece 26 which is in fluid communication with the air chamber 20 in the main body 18 and through which a user exhales to actuate the substance supply unit 22, as will be described in more detail hereinbelow.

The delivery unit 4 further comprises a trigger mechanism 30 which is configured to be actuatable to cause actuation of the substance supply unit 22. In this embodiment the trigger mechanism 30 is configured to be actuatable to cause actuation of the substance supply unit 22 on generation of a predetermined pressure within the air chamber 20 in the main body 18. In an alternative embodiment the trigger mechanism 30 could be configured to be actuatable to cause actuation of the substance supply unit 22 on generation of a predetermined flow rate through the mouthpiece 26.

The trigger mechanism 30 includes first and second latching members 34, 35 and first and second resilient elements 36, 37 which act to bias respective ones of the first and second latching members 34, 35 radially outwardly with respect to the delivery unit 4 to a latching position, in which position the first and second latching members 34, 35 are located in respective ones of the first and second latching apertures 14, 16 in the tubular member 8 of the housing 2, and thereby provide a user with an indication that the nosepiece 10 is sufficiently inserted into a nostril of a user for effective operation of the delivery device. The first latching member 34 includes an aperture 38 therein for accommodating a link 42, as will be described in more detail hereinbelow. With the delivery unit 4 in other than the delivery position, that is, not biased to the delivery position, the latching members 34, 35 are not located in the respective ones of the latching apertures 14, 16, thereby providing an indication to a user that the nosepiece 10 is not sufficiently inserted for effective operation of the delivery device. With the delivery unit 4 in the delivery position, that is, biased sufficiently that the nosepiece 10 is sufficiently inserted for effective operation of the delivery device, the latching members 34, 35 are located in the respective ones of the latching apertures 14, 16, thereby providing an indication to a user that the nosepiece 10 is sufficiently inserted for effective operation, and hence ready for actuation by exhaling through the mouthpiece 26. Following actuation of the substance supply unit 22, the latching members 34, 35 can be released from the respective ones of the latching apertures 14, 16, and hence the delivery unit 4 returned to the rest position, by depressing the latching members 34, 35; the delivery unit 4 being returned to the rest position by the action of the biasing element 6.

Figure 7D:
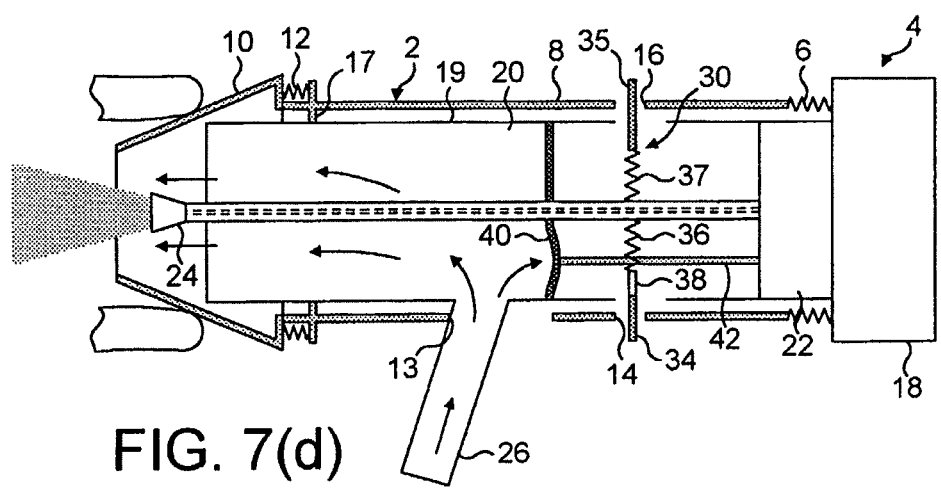
FIG. 7(d) schematically illustrates the nasal delivery device of FIG. 7(a) in an actuated configuration.

The trigger mechanism 30 further includes a flexible member 40, in this embodiment a resilient membrane, which defines a part of the wall of the air chamber 20 in the main body 18, and a link 42 which extends through the aperture 38 in the first latching member 34 and couples the flexible member 40 and the release mechanism of the substance supply unit 22. The flexible member 40 is configured such as, on generation of a predetermined actuation pressure within the air chamber 20 in the main body 18, to be deflected sufficiently as to actuate the release mechanism of the substance supply unit 22, and thereby deliver a metered dose of a substance (as illustrated in FIG. 7(d)). This actuation pressure cannot be achieved until the tubular member 8 of the housing 2 has been biased into sealing engagement with the nosepiece 10 (as illustrated in FIGS. 7(b) to (d)). Whilst the tubular member 8 of the housing 2 is not in sealing engagement with the nosepiece 10 (as illustrated in FIG. 7(a)), the exhalation breath of a user which is delivered through the mouthpiece 26 escapes from the aperture 12 between the tubular member 8 of the housing 2 and the nosepiece 10, thereby preventing the development of the actuation pressure within the air chamber 20 of the main body 18.

With this configuration, the actuation of the delivery device is prevented until a proper sealing fit is achieved to a nostril of a user. As will be understood, a sealing fit of the nosepiece 10 in a nostril of a user is essential for the proper operation of the delivery device, as otherwise optimal delivery, in particular bi-directional flow through the nasal cavities, would not be achieved. Also, as the delivery device is inoperable until properly fitted, the user learns intuitively to use the device properly. Moreover, the delivery device is operable even in the case of complete nasal obstruction, provided the nosepiece 10 is correctly positioned.

Figure 8A:
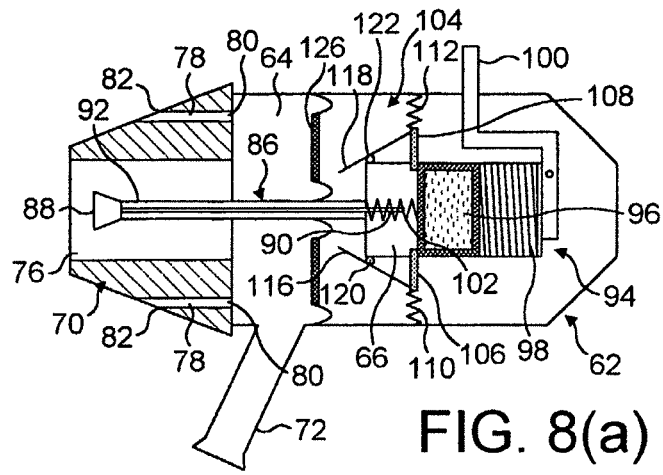
FIG. 8(a) schematically illustrates a nasal delivery device in accordance with a seventh embodiment of the present invention.
Figure 8B:
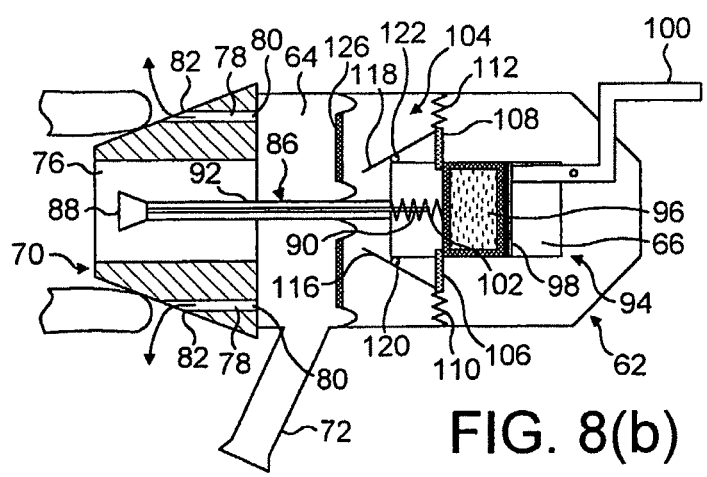
FIG. 8(b) schematically illustrates the nasal delivery device of FIG. 8(a) in a primed configuration.
Figure 8C:
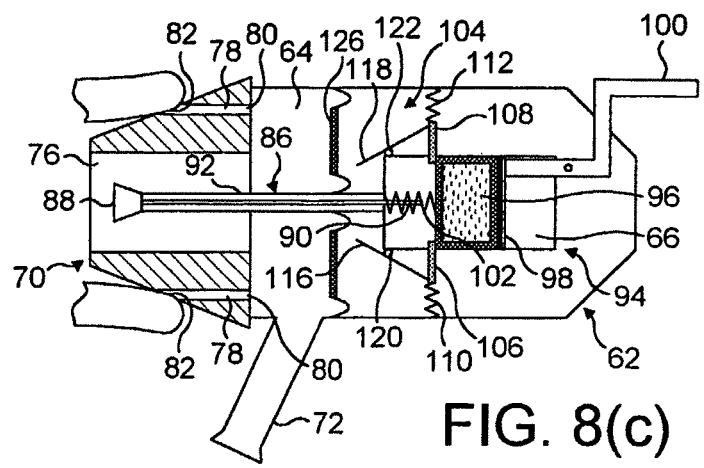
FIG. 8(c) schematically illustrates the nasal delivery device of FIG. 8(a) in an operative configuration.
Figure 8D:
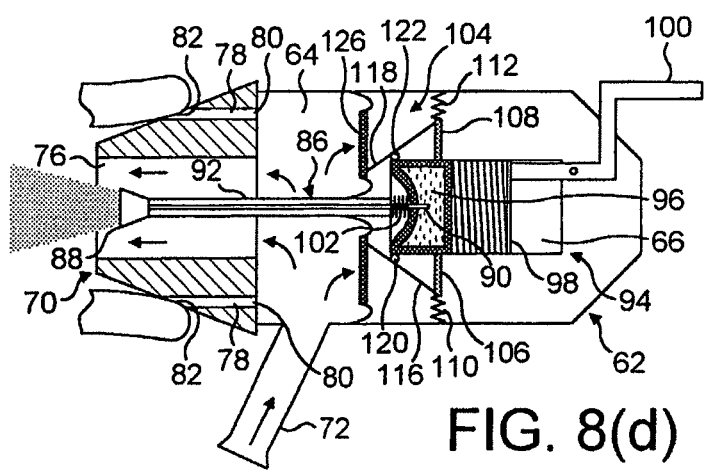
FIG. 8(d) schematically illustrates the nasal delivery device of FIG. 8(a) in an actuated configuration.

FIGS. 8(a) to (c) illustrate an exhalation breath-actuated nasal delivery device in accordance with a seventh embodiment of the present invention.

The delivery device comprises a housing 62 which includes a first, air chamber 64 for receiving the exhalation breath of a user and a second, cartridge chamber 66 for receiving a cartridge 96 containing a substance to be delivered, a nosepiece 70 for fitting in a nostril of a user which is in fluid communication with the air chamber 64 in the housing 62 and disposed to one, the distal, end of the housing 62, and a mouthpiece 72 through which the user exhales and which is in fluid communication with the air chamber 64 in the housing 62.

The nosepiece 70 includes a main channel 76, in this embodiment a central channel, and a plurality of secondary channels 78 which each include an inlet 80 in fluid communication with the air chamber 64 in the housing 62 and an outlet 82 at the outer surface of the nosepiece 70, in this embodiment disposed about the periphery thereof. The outlets 82 of the secondary channels 78 are located such as to be open when the nosepiece 70 is not sufficiently inserted in a nostril of a user for effective operation of the delivery device, thereby providing for the escape of exhaled air from the exhalation breath of a user directly to the atmosphere, and closed by a nostril of a user when the nosepiece 70 is sufficiently inserted in the nostril for effective operation of the delivery device. By providing for the escape of exhaled air from the exhalation breath of a user other than through the main channel 76 of the nosepiece 70 when the nosepiece 70 is not sufficiently inserted in a nostril of a user for effective operation of the delivery device, the pressure which can be developed in the air chamber 64 in the housing 62 by a user is insufficient to actuate the delivery device, as will be described in more detail hereinbelow. When the nosepiece 70 is sufficiently inserted in a nostril of a user for effective operation of the delivery device, the exhaled air from the exhalation breath of a user has no means of escape other than through the main channel 76 of the nosepiece 70, and thereby allows for actuation of the delivery device on generation of a predetermined actuation pressure within the air chamber 64 in the housing 62.

The delivery device further comprises a nozzle 86 for providing an aerosol spray through the main channel 76 of the nosepiece 70. The nozzle 86 comprises a head 88 which is located, in this embodiment co-axially, within the main channel 76 of the nosepiece 70, a tubular needle 90 which extends into one end, in this embodiment the forward end, of the cartridge chamber 66 in the housing 62, and a delivery tube 92 which fluidly connects the head 88 and the needle 90.

The delivery device further comprises a substance supply unit 94 for delivering a metered dose of a substance, in this embodiment a metered volume of a liquid containing medicament, either as a suspension or solution, to the nozzle 86.

The substance supply unit 94 comprises a cartridge 96 which is movable in the cartridge chamber 66 in the housing 62 between a first, loading position in which the cartridge 96 is not in fluid communication with the needle 90 of the nozzle 86 and a second, delivery position in which the cartridge 96 is in fluid communication with the needle 90 of the nozzle 86.

In this embodiment the cartridge 96 is a single-use cartridge which comprises a flexible container containing a volume of a substance, in this embodiment a liquid containing medicament, either as a suspension or solution. In use, cartridges 96 are loaded as required.

The substance supply unit 94 further comprises a first, main biasing element 98, in this embodiment a resilient element, particularly a compression spring, for biasing the cartridge 96 in a first, actuating direction when in the loading position, and a loading member 100, in this embodiment a lever, for loading the main biasing element 98 such as to bias the cartridge 96, when in the loading position, with an actuation force. The loading member 100 is movable between a first, rest position in which the main biasing element 98 is not loaded thereby, and a second, operative position in which the main biasing element 98, when restrained by the cartridge 96, loads the cartridge 96 with the actuation force.

The substance supply unit 94 further comprises a second, return biasing element 102, in this embodiment a resilient element, particularly a compression spring, for biasing the cartridge 96 in a second, return direction to return a used cartridge 96 from the delivery position to the loading position, and thereby allow for ready removal of the used cartridge 96.

The delivery device further comprises a trigger mechanism 104 which is configured to be actuatable to cause the actuation of the substance supply unit 94. In this embodiment the trigger mechanism 104 is configured to be actuatable to cause actuation of the substance supply unit 94 on generation of a predetermined pressure in the air chamber 64 in the housing 62. In an alternative embodiment the trigger mechanism 104 could be configured to be actuatable to cause actuation of the substance supply unit 94 on generation of a predetermined flow rate through the mouthpiece 72.

The trigger mechanism 104 comprises first and second stop members 106, 108, and first and second biasing elements 110, 112, in this embodiment resilient elements, particularly compression springs, which act to bias respective ones of the first and second stop members 106, 108 inwardly into the cartridge chamber 66 in the housing 62 to a stop position (as illustrated in FIGS. 8(a) and (b)) in which the first and second stop members 106, 108 act to prevent movement of the cartridge 96 from the loading position to the delivery position.

The trigger mechanism 104 further comprises first and second arms 116, 118 which are pivotable about respective pivots 120, 122 and coupled at one end thereof to respective ones of the first and second stop members 106, 108 such that pivoting of the arms 116, 118 to a release position causes the respective ones of the stop members 106, 108 to which the arms 116, 118 are coupled to be moved outwardly against the bias of the first and second biasing elements 110, 112 to a release position (as illustrated in FIG. 8(*c*)) in which the stop members 106, 108 are disposed outwardly of the cartridge chamber 66 in the housing 62 and out of engagement with the cartridge 96, such that the cartridge 96, when biased by the main biasing element 98, is driven to the delivery position. In being driven to the delivery position, the needle 90 of the nozzle 86 punctures the cartridge 96 such as to provide for fluid communication between the nozzle 86 and the cartridge 96, and, as the cartridge 96 is driven further, the cartridge 96 is collapsed to expel a metered dose of a substance therefrom through the nozzle 86.

The trigger mechanism 104 further comprises a diaphragm 126, in this embodiment a resilient member, which defines a part of the wall of the air chamber 64 in the housing 62. The diaphragm 126 is configured such as, on generation of a predetermined actuation pressure within the air chamber 64 in the housing 62, to be deflected such as to engage the other, distal ends of the arms 116, 118 and cause the same to be pivoted to the release position. This actuation pressure cannot be achieved until the nosepiece 70 is sufficiently inserted in a nostril of a user for effective operation of the delivery device, in which position the outlets 82 of the secondary channels 78 in the nosepiece 70 are closed by the nostril of the user and prevent the escape of exhaled air from the exhalation breath of the user directly to the atmosphere. Whilst the outlets 82 of the secondary channels 78 in the nosepiece 70 are open, exhaled air from the exhalation breath of a user escapes to the atmosphere, thereby preventing the development of the actuation pressure within the air chamber 64 in the housing 62.

With this configuration, the actuation of the delivery device is prevented until a proper sealing fit is achieved to a nostril of a user. As will be understood, a sealing fit of the nosepiece 70 in a nostril of a user is essential for the proper operation of the delivery device, as otherwise optimal delivery, in particular bi-directional flow through the nasal cavities, would not be achieved. Also, as the delivery device is inoperable until properly fitted, a user learns intuitively to use the device properly. Moreover, the delivery device is operable even in the case of complete nasal obstruction, provided the nosepiece 70 is correctly positioned.

FIGS. 9(*a*) to (*c*) illustrate an exhalation breath-actuated nasal delivery device in accordance with an eighth embodiment of the present invention.

The delivery device comprises a housing 132 which includes an air chamber 134 for receiving the exhalation breath of a user, a nosepiece 140 for fitting in a nostril of a user which is in fluid communication with the air chamber 134 in the housing 132 and disposed to one, the distal, end of the housing 132, and a mouthpiece 142 through which a user exhales and which is in fluid communication with the air chamber 134 in the housing 132.

The nosepiece 140 comprises a substantially rigid inner tubular member 144 which defines a main channel 146 therethrough, and a flexible outer tubular member 148, in this embodiment a resilient member, which is disposed about, in this embodiment co-axially with, the inner tubular member 144 and defines an annular conduit 150 at the periphery of the nosepiece 140 which is in fluid communication with the air chamber 134 in the housing 132. The outer tubular member 148 is configured to be sufficiently flexible as not to provide tight seal against a nostril of a user when the nosepiece 140 is other than sufficiently inserted into the nostril of the user as to provide for effective operation of the delivery device. When the nosepiece 140 is not sufficiently inserted into a nostril of a user, a flow path exists between the outer surface of the outer tubular member 148 and the nostril of the user, thereby providing for the escape of exhaled air from the exhalation breath of a user. When the nosepiece 140 is sufficiently inserted into a nostril of a user as to provide for effective operation of the delivery device, the outer tubular member 148 provides a fluid tight seal with the nostril of the user, thereby preventing the escape of the exhalation breath of a user and allowing for actuation of the delivery device on generation of a predetermined actuation pressure within the air chamber 134 in the housing 132. In this embodiment the outer tubular member 148 is a resilient member which normally adopts a position spaced from the inner tubular member 144 (as illustrated in FIGS. 9(*a*) and (*b*)) and is compressed on insertion into a nostril of a user to close the annular conduit 148 (as illustrated in FIG. 9(*c*)).

The delivery device further comprises a nozzle 154 for providing an aerosol spray from the nosepiece 140. The nozzle 154 comprises a head 156 which is located, in this embodiment co-axially, with the main channel 146 of the nosepiece 140, and a delivery tube 158 in fluid communication with the head 156.

The delivery device further comprises a substance supply unit 160 for delivering a metered dose of a substance, in this embodiment a metered volume of a liquid containing medicament, either as a suspension or solution, to the nozzle 154.

The substance supply unit 160 comprises a substance chamber 162 which contains a volume of a substance, in this embodiment a liquid containing medicament, either as a suspension or solution. The substance chamber 162 includes an aperture 164 which is sealed by a rupturable seal 166 and in fluid communication with the delivery tube 158 of the nozzle 154. The rupturable seal 166 is configured such as to be ruptured on the application of pressure to the substance in the substance chamber 162 in delivering substance therefrom, whereby substance is delivered from the substance chamber 162 to the nozzle 154.

The substance supply unit 160 further comprises a piston 168 which is slideable in the substance chamber 162 between a first, containing position (as illustrated in FIGS. 9(*a*) to (*c*)) in which a volume of a substance is contained in the substance chamber 162 and a second, dosed position (as illustrated in FIG. 9(*d*)) in which a metered dose of the substance has been expelled therefrom through the nozzle 154. The piston 168 includes a peripheral groove 170, the purpose of which will be described in detail hereinbelow. In driving the piston 168 to the dosed position, the seal 166 at the aperture 164 in the substance chamber 162 is ruptured such as to provide for fluid communication between the nozzle 154 and the substance chamber 162, and, as the piston 168 is driven further, a metered dose of a substance is expelled from the substance chamber 162 through the nozzle 86 to provide a metered aerosol spray from the delivery device.

The substance supply unit 160 further comprises a biasing element 172, in this embodiment a resilient element, particularly a compression spring, for biasing the piston 168 in an actuating direction when in the containing position, and a loading member 174, in this embodiment a lever, for loading the biasing element 172 such as to bias the piston 168 in the containing position with an actuation force. The loading member 174 is movable between a first, inoperative position (as illustrated in FIG. 9(*a*)) in which the biasing element 172 is not loaded thereby, and a second, operative position (as illustrated in FIGS. 9(b) and (c)) in which the biasing element 172, when restrained by the piston 168, loads the piston 168 with the actuation force.

The delivery device further comprises a trigger mechanism 184 which is configured to be actuatable to cause the actuation of the substance supply unit 160. In this embodiment the trigger mechanism 184 is configured to be actuatable to cause the actuation of the substance supply unit 184 on generation of a predetermined actuation pressure in the air chamber 134 in the housing 132. In an alternative embodiment the trigger mechanism 184 could be configured to be actuatable to cause the actuation of the substance supply unit 184 on generation of a predetermined flow rate through the mouthpiece 142.

Figure 9A:
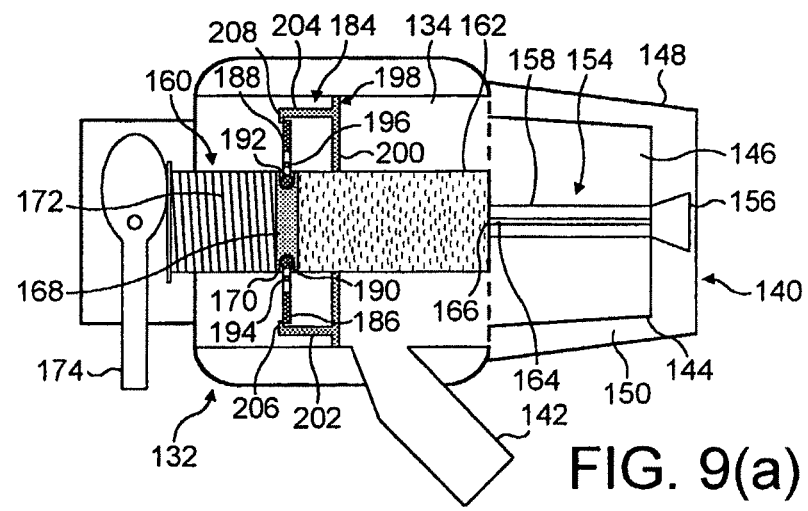
FIG. 9(a) schematically illustrates a nasal delivery device in accordance with an eighth embodiment of the present invention.
Figure 9B:
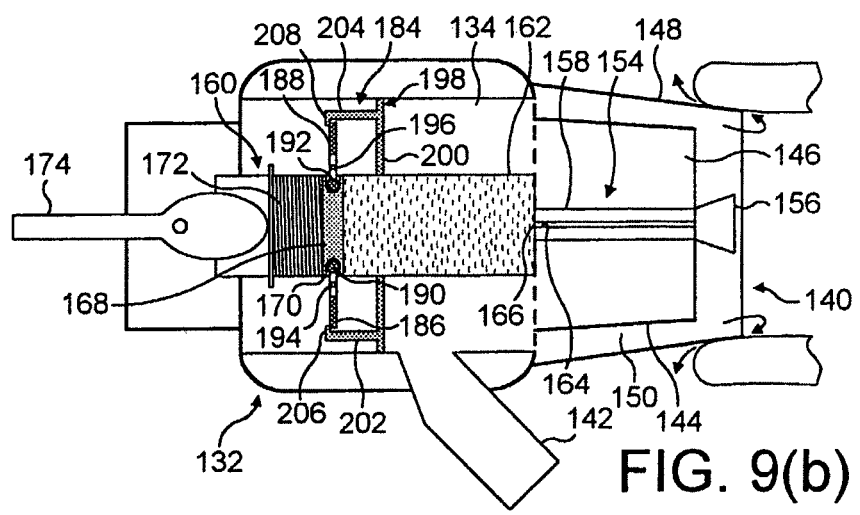
FIG. 9(b) schematically illustrates the nasal delivery device of FIG. 9(a) in a primed configuration.
Figure 9C:
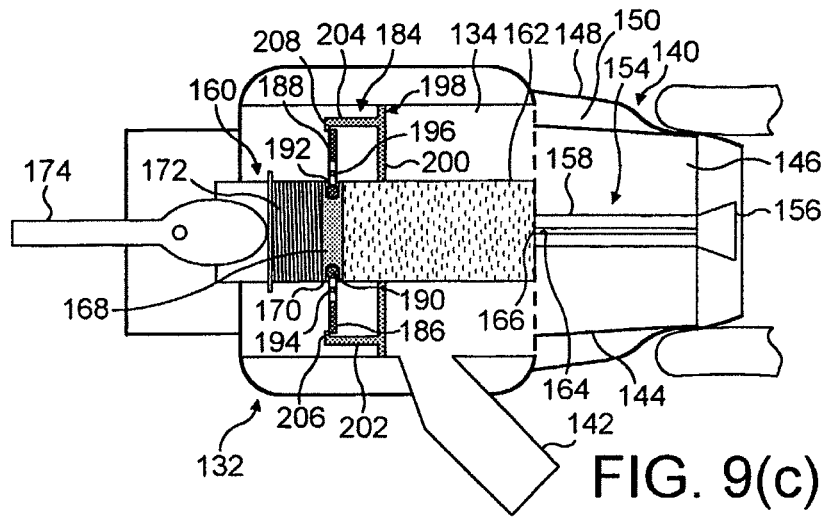
FIG. 9(c) schematically illustrates the nasal delivery device of FIG. 9(a) in an operative configuration.

The trigger mechanism 184 comprises first and second locking members 186, 188, in this embodiment disposed at opposite sides of the substance chamber 162, which, when in a first, locking position (as illustrated in FIGS. 9(a) to (c)), act to prevent movement of the piston 168 from the containing position to the dosed position. The locking members 186, 188 each include a detent 190, 192 at one, the inner, end thereof, which detents 190, 192 engage in the groove 170 in the piston 168 when the locking members 186, 188 are in the locking position. The locking members 186, 188 are pivotable about a respective pivot 194, 196 between the first, locking position (as illustrated in FIGS. 9(a) to (c)) and a second, release position (as illustrated in FIG. 9(d)) in which the piston 168 is free to be driven under the action of the biasing element 172 to the dosed position.

Figure 9D:
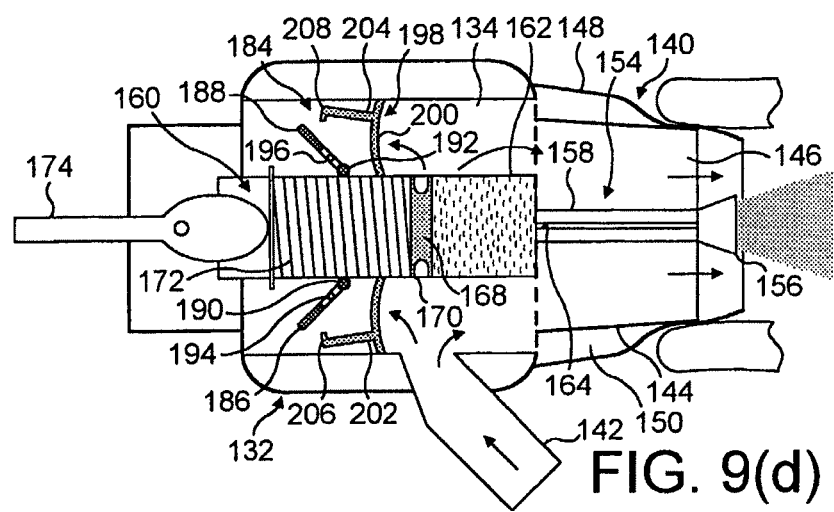
FIG. 9(d) schematically illustrates the nasal delivery device of FIG. 9(a) in an actuated configuration.
Figure 10A:
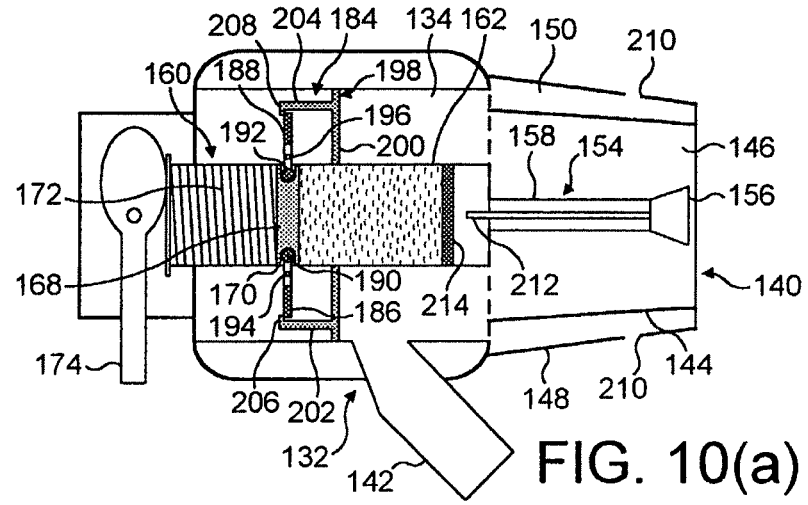
FIG. 10(a) schematically illustrates a nasal delivery device in accordance with an ninth embodiment of the present invention.
Figure 10B:
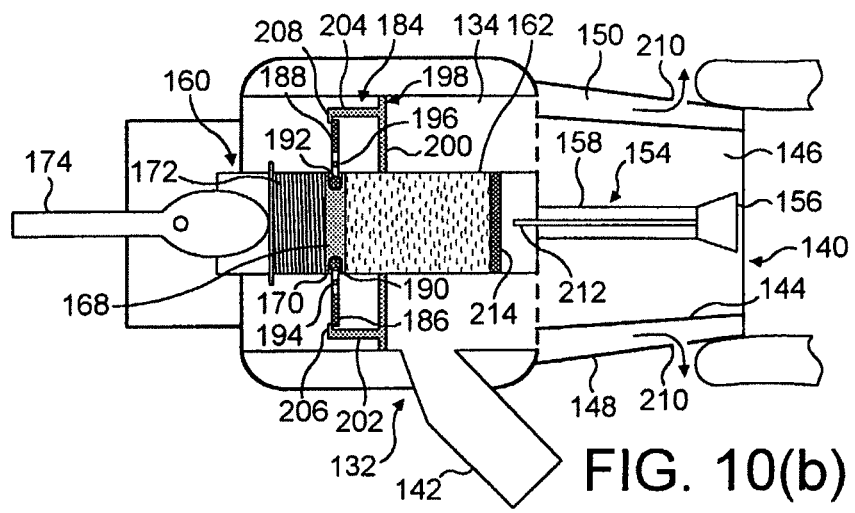
FIG. 10(b) schematically illustrates the nasal delivery device of FIG. 10(a) in a primed configuration.
Figure 10C:
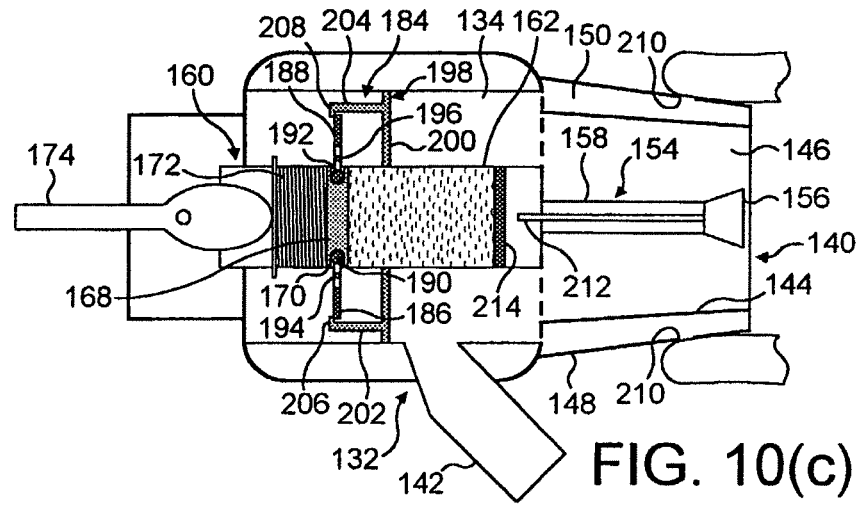
FIG. 10(c) schematically illustrates the nasal delivery device of FIG. 10(a) in an operative configuration.
Figure 10D:
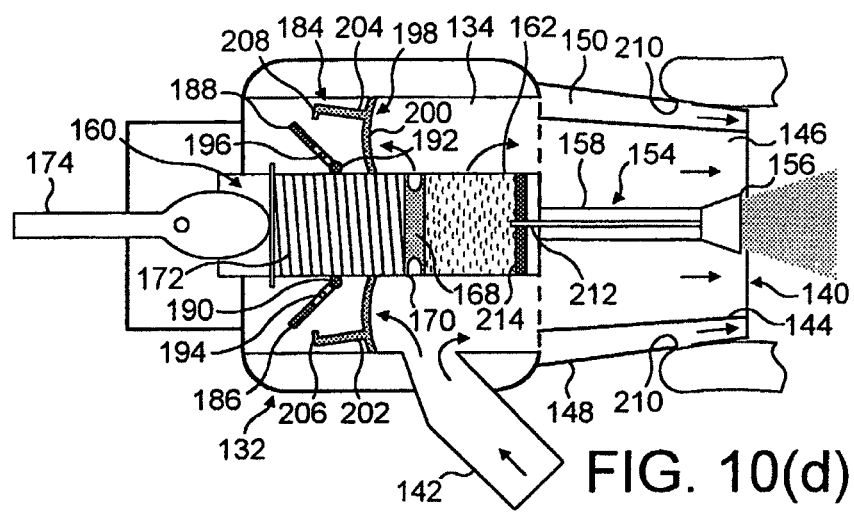
FIG. 10(d) schematically illustrates the nasal delivery device of FIG. 10(a) in an actuated configuration.
Figure 11A:
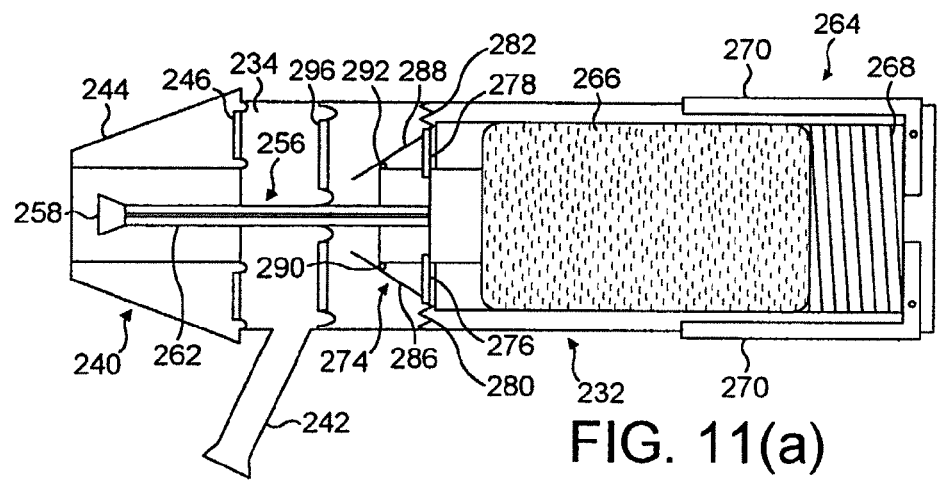
FIG. 11(a) schematically illustrates a nasal delivery device in accordance with a tenth embodiment of the present invention.
Figure 11B:
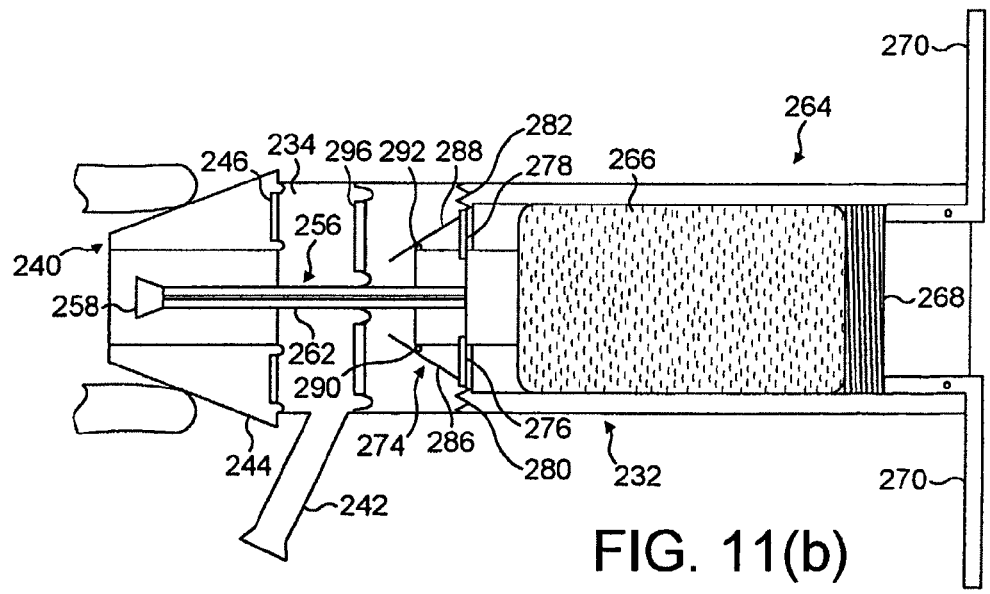
FIG. 11(b) schematically illustrates the nasal delivery device of FIG. 11(a) in a primed, but inoperative configuration.
Figure 11C:
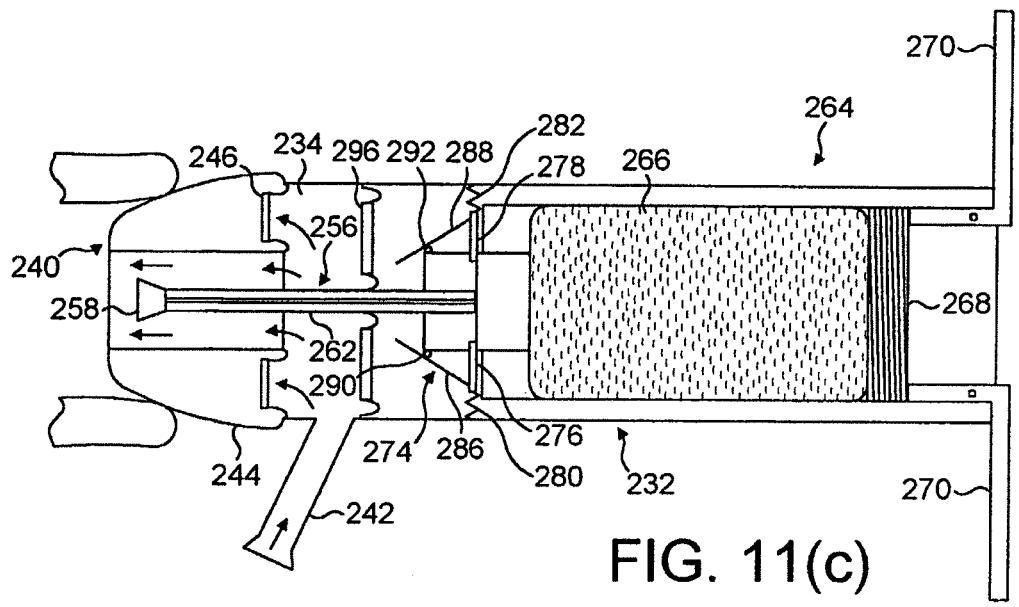
FIG. 11(c) schematically illustrates the nasal delivery device of FIG. 11(a) in an operative configuration.
Figure 11D:
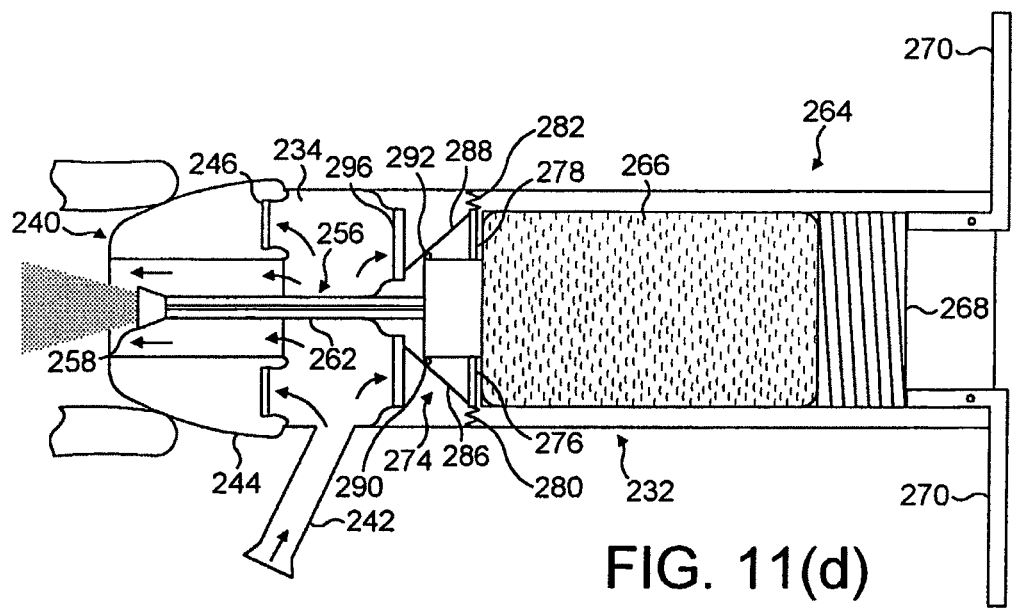
FIG. 11(d) schematically illustrates the nasal delivery device of FIG. 11(a) in an actuated configuration.
Figure 12A:
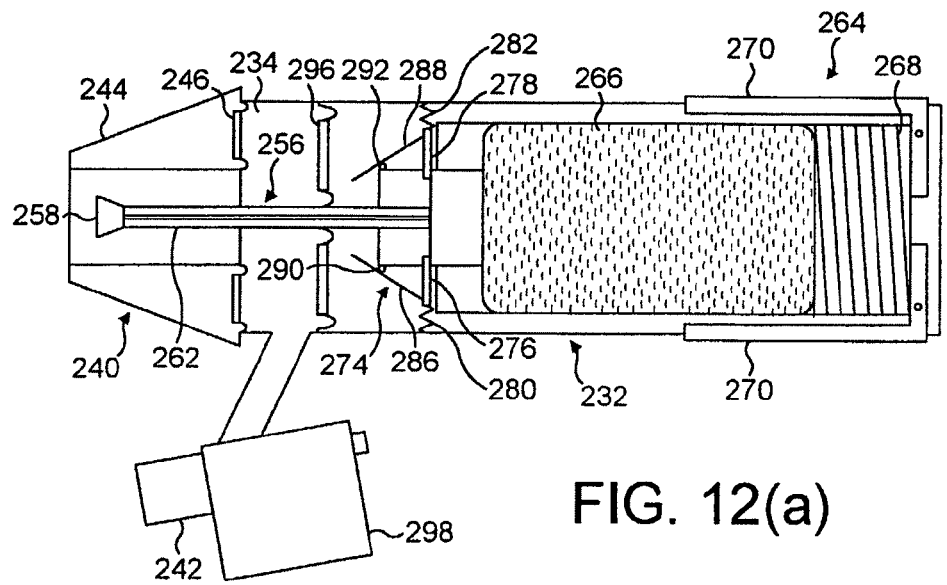
FIG. 12(a) schematically illustrates a nasal delivery device in accordance with an eleventh embodiment of the present invention.
Figure 12B:
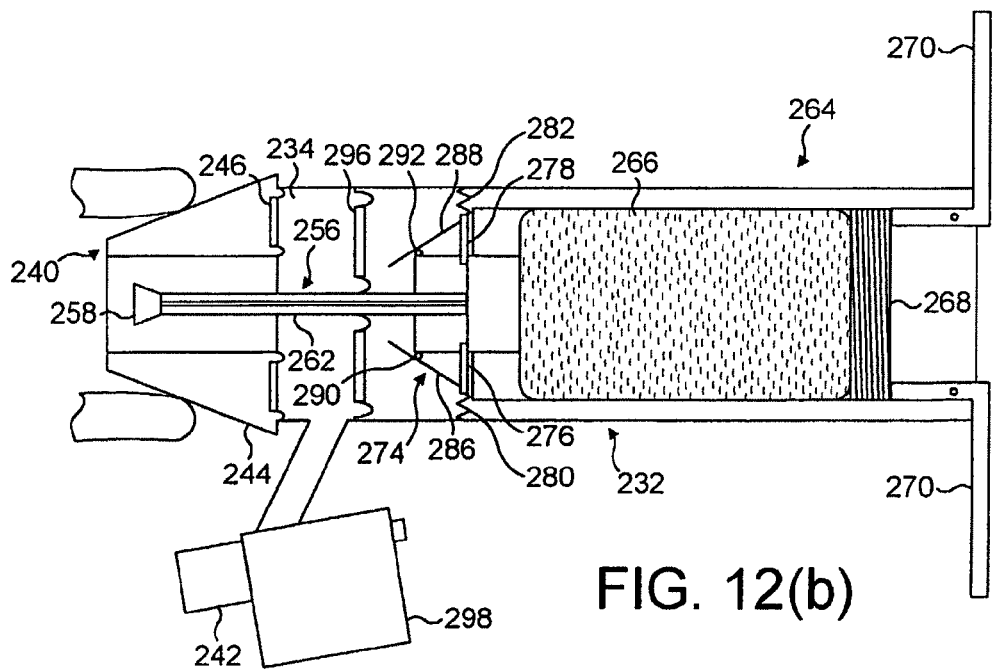
FIG. 12(b) schematically illustrates the nasal delivery device of FIG. 12(a) in a primed, but inoperative configuration.
Figure 12C:
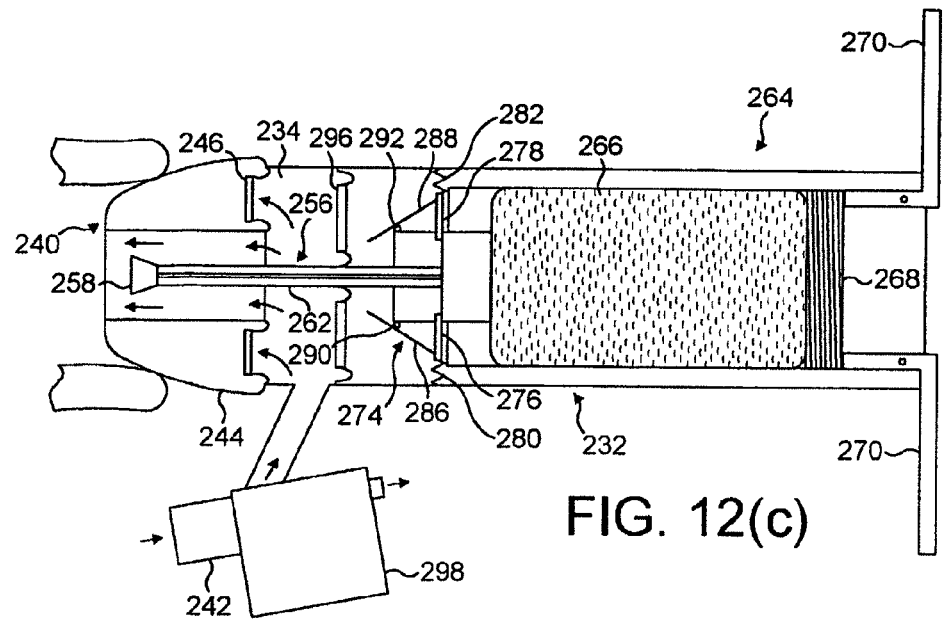
FIG. 12(c) schematically illustrates the nasal delivery device of FIG. 12(a) in an operative configuration.
Figure 12D:
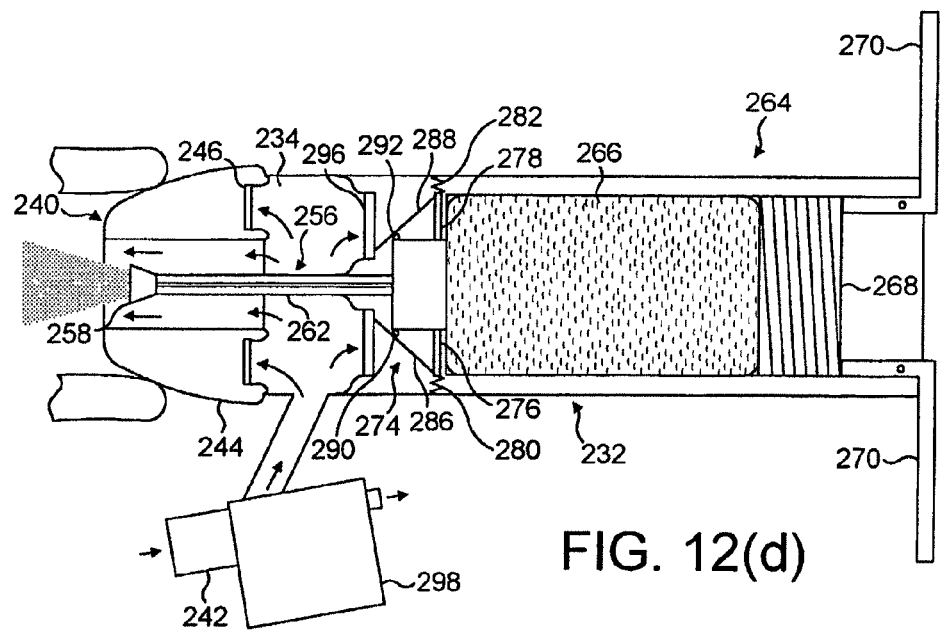
FIG. 12(d) schematically illustrates the nasal delivery device of FIG. 12(a) in an actuated configuration.

The trigger mechanism 184 further comprises a latching unit 198 which, in a first, latching position (as illustrated in FIGS. 9(a) and (b)), acts to retain the stop members 186, 188 in the locking position and, in a second, release position (as illustrated in FIG. 9(d)), releases the locking members 186, 188 to allow the locking members 186, 188 to be released from the locking position.

The latching unit 198 comprises a flexible member 200, in this embodiment a resilient membrane, which defines a part of the wall of the air chamber 134 in the housing 132 and is configured to be deflected by the air pressure developed in the air chamber 134 in the housing 132. The flexible member 200 is configured such as to be deflected sufficiently on the generation of a predetermined actuation pressure within the air chamber 134 in the housing 132 that the latching unit 198 adopts the release position.

The latching unit 198 further comprises first and second arms 202, 204 which are attached to the flexible member 200 and include first and second latching projections 206, 208 which, when the latching unit 198 is in the latching position, engage the other, free ends of the respective ones of the locking members 186, 188 to retain the same in the locking position. The first and second arms 202, 204 are configured such that, when the flexible member 200 is deflected by the generation of an increased pressure in the air chamber 134 in the housing 132 by exhalation by a user through the mouthpiece 142, the first and second arms 202, 204 are pivoted outwardly. On the generation of a predetermined actuation pressure within the air chamber 134 in the housing 132, the arms 202, 204 are pivoted such that the latching projections thereof 206, 208 are released from engagement with the respective ones of the locking members 186, 188 (as illustrated from FIG. 9(c)), whereby the locking members 186, 188 are released from the locking position and the piston 168 is free to be driven from the containing position to the dosed position under the action of the resilient element 172. This actuation pressure cannot be achieved until the nosepiece 140 is sufficiently inserted in a nostril of a user, in which position the outer tubular member 148 of the nosepiece 140 engages the inner tubular member 144 of the nosepiece 140 and the escape of exhaled air from the exhalation breath of a user directly to the atmosphere is prevented. Whilst the outer tubular member 148 of the nosepiece 140 does not engage the inner tubular member 144 of the nosepiece 140, the exhalation breath of a user escapes to the atmosphere about the outer surface of the outer tubular member 148, thereby preventing the development of the predetermined actuation pressure within the air chamber 134 in the housing 132.

With this configuration, the actuation of the delivery device is prevented until a proper sealing fit is achieved to a nostril of a user. As will be understood, a sealing fit of the nosepiece 140 in the nostril of a user is essential for the proper operation of the delivery device, as otherwise optimal delivery, in particular bi-directional flow through the nasal cavities, would not be achieved. Also, as the delivery device is inoperable until properly fitted, a user learns intuitively to use the device properly. Moreover, the delivery device is operable even in the case of complete nasal obstruction, provided the nosepiece 140 is correctly positioned.

FIGS. 10(a) to (d) illustrate an exhalation breath-actuated nasal delivery device in accordance with a ninth embodiment of the present invention.

The nasal delivery device of this embodiment is very similar to the nasal delivery device of the above-described eighth embodiment, and thus, in order to avoid unnecessary duplication of description, only the differences will be described in detail, with like reference signs designating like parts.

The nasal delivery device of this embodiment differs from that of the above-described eighth embodiment in the construction of the nosepiece 140, the nozzle 154 and the substance supply unit 162.

In this embodiment the outer tubular member 148 of the nosepiece 140 is a rigid member and includes a plurality of apertures 210, in this embodiment disposed about the periphery thereof, with each of the apertures 210 defining an outlet at the outer surface of the nosepiece 140. The apertures 210 are located such as to be open when the nosepiece 140 is not sufficiently inserted in a nostril of a user for effective operation of the delivery device, thereby providing for the escape of exhaled air from the exhalation breath of a user directly to the atmosphere, and closed by a nostril of a user when the nosepiece 140 is sufficiently inserted in the nostril for effective operation of the delivery device. By providing for the escape of exhaled air from the exhalation breath of a user other than through the nostril of the user when the nosepiece 140 is not sufficiently inserted in a nostril of the user for effective operation of the delivery device, the pressure which can be developed in the air chamber 134 in the housing 132 by the user is insufficient to actuate the delivery device, as will be described in more detail hereinbelow. When the nosepiece 140 is sufficiently inserted in a nostril of a user for effective operation of the delivery device, the exhaled air from the exhalation breath of the user has no means of escape other than through the nostril of the user, and thereby allows for actuation of the delivery device on generation of a predetermined actuation pressure within the air chamber 134 in the housing 132.

In this embodiment the nozzle 154 further comprises a tubular needle 212 which extends into one end, in this embodiment the forward end, of the substance chamber 162 and is in fluid communication with the delivery tube 158.

In this embodiment the substance supply unit 160 comprises, in place of the rupturable seal 166, a second piston 214 which is disposed in the substance chamber 162 forwardly of the first piston 168, with the spacing of the pistons 168, 214 defining the volume of substance contained in the substance chamber 162, and hence the metered dose to be delivered by the delivery device. With this configuration, the second piston 214 is driven forwardly on the first piston 168 being driven forwardly under the bias of the biasing element 172, the substance contained by the pistons 168, 214 being substantially incompressible. The second piston 214 is a puncturable member which is punctured by the needle 212 of the nozzle 154 on being driven onto the same, with the needle 212 of the nozzle 154 being in fluid communication with the volume of substance contained between the pistons 168, 214 on puncturing the second piston 214.

Operation of the delivery device is the same as for the delivery device of the above-described eighth embodiment, with a user being able to exhale through the mouthpiece 142, but the trigger mechanism 184 not being operable, and hence the substance supply unit 160 not being actuatable, until the delivery device is sufficiently inserted into a nostril of the user for effective operation of the delivery device.

FIGS. 11(*a*) to (*d*) illustrate an exhalation breath-actuated nasal delivery device in accordance with a tenth embodiment of the present invention.

The delivery device comprises a housing 232 which includes an air chamber 234 for receiving the exhalation breath of a user, a nosepiece 240 for fitting in a nostril of a user which is in fluid communication with the air chamber 234 in the housing 232 and disposed to one, the distal, end of the housing 232, and a mouthpiece 242 through which the user exhales and which is in fluid communication with the air chamber 234 in the housing 232.

The nosepiece 240 is an expandable member which is configured to expand on exhalation through the mouthpiece 242 such as to promote a sealing fit between the nosepiece 240 and a nostril of a user, with such a sealing fit only being achievable on the nosepiece 240 firstly being sufficiently inserted into a nostril of a user for effective operation of the delivery device. Where the nosepiece 240 is not sufficiently inserted into a nostril of a user for effective operation of the delivery device, exhaled air from the exhalation breath of the user escapes to the atmosphere between the outer peripheral surface of the nosepiece 240 and the nostril of the user. In this embodiment the nosepiece 240 comprises an enclosed, gas-filled annular member, the outer surface 244 and at least a part of the inner surface 246 of which are flexible elements, in this embodiment resilient elements, such that the pressure generated in the air chamber 234 in the housing 232 by the exhalation breath of a user acts on the inner surface 246 of the nosepiece 240 to cause the outer surface 244 of the nosepiece 240 to expand outwardly into contact with the nostril of the user, and thereby both seal the nosepiece 240 to the nostril of the user and expand the nostril, and hence nasal airway, of the user. By providing for the escape of exhaled air from the exhalation breath of a user other than through the nostril of the user when the nosepiece 240 is not sufficiently inserted in the nostril of the user for effective operation of the delivery device, the pressure which can be developed in the air chamber 234 in the housing 232 by the user is insufficient to actuate the delivery device, as will be described in more detail hereinbelow. When the nosepiece 240 is sufficiently inserted in a nostril of a user for effective operation of the delivery device, the exhaled air from the exhalation breath of a user has no means of escape other than through the nostril of the user, and thereby allows for actuation of the delivery device on generation of a predetermined actuation pressure within the air chamber 234 in the housing 232.

The delivery device further comprises a nozzle 256 for providing an aerosol spray through the nosepiece 240. The nozzle 256 comprises a head 258 which is located, in this embodiment co-axially, within the nosepiece 240, and a delivery tube 262 which is fluidly connected to the head 258.

The delivery device further comprises a substance supply unit 264 for delivering a metered dose of a substance, in this embodiment a metered volume of a liquid containing medicament, either as a suspension or solution, to the nozzle 256.

In this embodiment the substance supply unit 264 comprises a mechanical delivery pump 266, in particular a liquid delivery pump or a powder delivery pump, which is coupled to the nozzle 256 and is configured, on actuation, to deliver a metered dose of a substance, in this embodiment a liquid containing medicament, either as a suspension or solution, as an aerosol spray. The delivery pump 266 is movable relative to the nozzle 256 from a first, non-actuated position (as illustrated in FIGS. 11(*a*) to (*c*)) to a second, actuated position (as illustrated in FIG. 11(*d*)) in which a metered dose of substance has been delivered.

In an alternative embodiment the substance supply unit 264 comprises an aerosol canister for delivering metered volumes of a propellant, preferably a hydrofluoroalkane (HFA) propellant or the like, containing medicament.

The substance supply unit 264 further comprises a biasing element 268, in this embodiment a resilient element, particularly a compression spring, for biasing the delivery pump 266 in an actuating direction when in the non-actuated position, and a loading member 270, in this embodiment first and second levers, for loading the biasing element 268 such as to bias the delivery pump 266, when in the non-actuated position, with an actuation force. The loading member 270 is movable between a first, rest position in which the biasing element 268 is not loaded thereby, and a second, operative position in which the biasing element 268, when restrained by the delivery pump 266, loads the delivery pump 266 with the actuation force.

The delivery device further comprises a trigger mechanism 274 which is configured to be actuatable to cause the actuation of the substance supply unit 264. In this embodiment the trigger mechanism 274 is configured to be actuatable to cause actuation of the substance supply unit 264 on generation of a predetermined pressure in the air chamber 234 in the housing 232. In an alternative embodiment the trigger mechanism 274 could be configured to be actuatable to cause actuation of the substance supply unit 264 on generation of a predetermined flow rate through the mouthpiece 242.

The trigger mechanism 274 comprises first and second stop members 276, 278, and first and second biasing elements 280, 282, in this embodiment resilient elements, particularly compression springs, which act to bias respective ones of the first and second stop members 276, 278 inwardly to a stop position (as illustrated in FIGS. 11(*a*) to (*c*)) in which the first and second stop members 276, 278 act to prevent movement of the delivery pump 266 from the non-actuated position to the actuated position.

The trigger mechanism 274 further comprises first and second arms 286, 288 which are pivotable about respective pivots 290, 292 and coupled at one end thereof to respective ones of the first and second stop members 276, 278 such that pivoting of the arms 286, 288 to a release position causes the respective ones of the stop members 276, 278 to which the arms 286, 288 are coupled to be moved outwardly against the bias of the first and second biasing elements 280, 282 to a release position (as illustrated in FIG. 11(*d*)) in which the stop members 276, 278 are disposed outwardly of the head of the delivery pump 266, such that the delivery pump 266, when biased by the biasing element 268, is driven to the actuated position. In being driven to the actuated position, a metered dose of a substance is delivered from the nozzle 256 as an aerosol spray.

The trigger mechanism 274 further comprises a diaphragm 296, in this embodiment a resilient member, which defines a part of the wall of the air chamber 234 in the housing 232. The diaphragm 296 is configured such as, on generation of a predetermined actuation pressure within the air chamber 234 in the housing 232, to be deflected such as to engage the other, distal ends of the arms 286, 288 and cause the same to be pivoted to the release position. This actuation pressure cannot be achieved until the nosepiece 240 is sufficiently inserted in a nostril of a user for effective operation of the delivery device, in which position the escape of exhaled air from the exhalation breath of the user directly to the atmosphere is prevented. Whilst the nosepiece 240 is not sufficiently inserted into a nostril of a user as to provide for effective operation of the delivery device, exhaled air from the exhalation breath of a user escapes to the atmosphere, thereby preventing the development of the actuation pressure within the air chamber 234 in the housing 232.

With this configuration, the actuation of the delivery device is prevented until a proper sealing fit is achieved to a nostril of a user. As will be understood, a sealing fit of the nosepiece 240 in a nostril of a user is essential for the proper operation of the delivery device, as otherwise optimal delivery, in particular bi-directional flow through the nasal cavities, would not be achieved. Also, as the delivery device is inoperable until properly fitted, a user learns intuitively to use the device properly. Moreover, the delivery device is operable even in the case of complete nasal obstruction, provided the nosepiece 240 is correctly positioned.

In this embodiment the positive pressure induced by a subject when producing bi-directional flow through the nasal cavities is used to provide for improved sealing with a nostril and at the same time expand the nasal valve, which nasal valve is the region of smallest cross-sectional area in the nasal passageway and thus represents the flow-limiting region. A large fraction of aerosol particles with an aerodynamic diameter exceeding 8 μm are deposited in the nasal passageway, especially in the anteriormost region of the nasal cavity, that is, the nasal valve. The nasal valve is framed by nasal cartilage and its cross-sectional area is the smallest in the nasal cavity. Expansion of the anteriorly located constriction significantly improves the deposition pattern by reducing the high deposition in the region of the constriction. By using the above-described nosepiece, the nasal valve is expanded progressively with increasing resistance of a nasal airway, that is, smaller dimension. Release of an aerosol through this expanded region enhances the aerosol deposition in the nasal turbinates and meatus compared to a traditional spray {Majima 1998 ID:4047}. Owing to the turbulence occurring at or immediately downstream of the nasal valve, a large fraction of drug is deposited in that region. The anterior region in lined with squamous epithelium (skin) and is not the target for topical or systemic drugs. By expanding the anterior nasal valve, which normally represents the narrowest part and highest resistance of the nasal airway, the point of highest resistance is moved to a more posterior region which is the target region to the present invention and is lined by mucosa.

FIGS. 12(*a*) to (*d*) illustrate an exhalation breath-actuated delivery device in accordance with an eleventh embodiment of the present invention.

The delivery device of this embodiment is very similar to the delivery device of the above-described tenth embodiment, and thus, in order to avoid unnecessary duplication of description, only the differences will be described in detail, with like reference signs designating like parts The delivery device of this embodiment differs from that of the above-described tenth embodiment in further comprising an exhalation breath actuatable gas delivery unit 298 for delivering a gas flow to the chamber 232 in the housing 234 in response to exhalation by a subject, and in that the mouthpiece 242 is in fluid communication with the gas delivery unit 298 and not the chamber 234 in the housing 232, whereby a gas flow separate from the exhalation breath of a subject is delivered to the chamber 234 in the housing 232, and hence the nasal airway, in response to exhalation through the mouthpiece 242.

Operation of the delivery device is the same as for the above-described first embodiment, with a gas flow being delivered to the chamber 234 in the housing 232, and hence a gas flow being developed in the nasal airway, in response to exhalation through the mouthpiece 242.

Figure 13A:
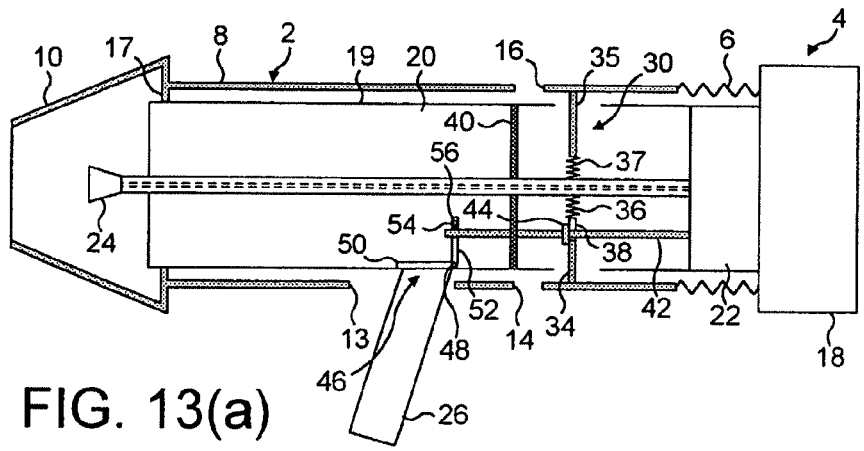
FIG. 13(a) schematically illustrates a nasal delivery device in accordance with a twelfth embodiment of the present invention.
Figure 13B:
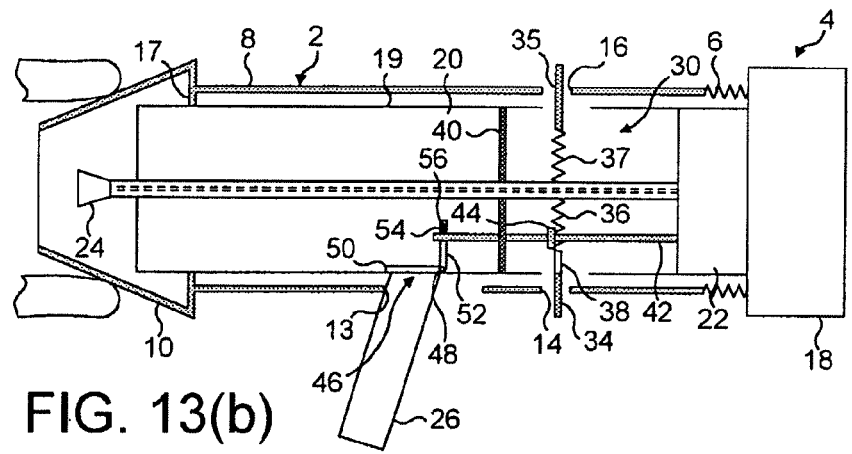
FIG. 13(b) schematically illustrates the nasal delivery device of FIG. 13(a) in an operative configuration.
Figure 13C:
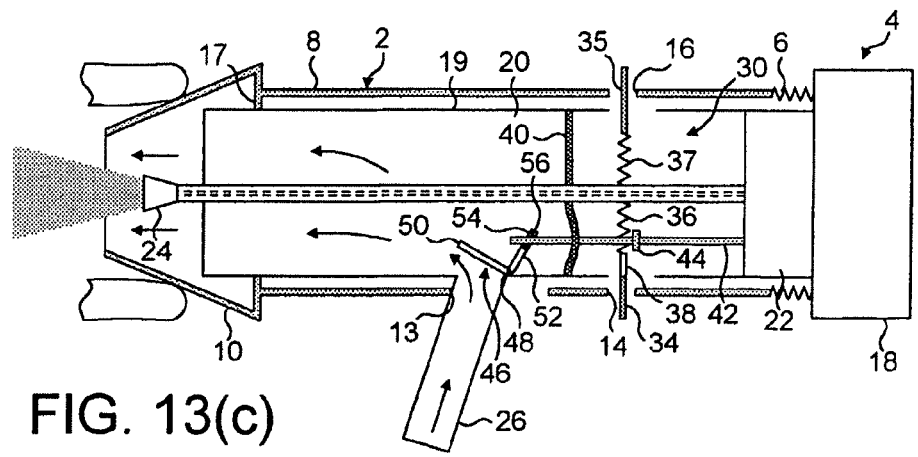
FIG. 13(c) schematically illustrates the nasal delivery device of FIG. 13(a) in an actuated configuration.

FIGS. 13(*a*) to (*c*) illustrate an exhalation breath-actuated nasal delivery device in accordance with a twelfth embodiment of the present invention.

The nasal delivery device of this embodiment is very similar to the nasal delivery device of the above-described fifth embodiment, and thus, in order to avoid unnecessary duplication of description, only the differences will be described in detail, with like reference signs designating like parts.

The nasal delivery device of this embodiment differs from that of the above-described fifth embodiment in that the trigger mechanism 30 includes the flexible member 40 of the above-described third embodiment, of which the fifth embodiment is a modification.

By incorporating both the flexible member 40 which is responsive to a pressure in the chamber 20 in the tubular member 19 to drive the link 42 and hence actuate the substance supply unit 22 on the development of a predetermined actuation pressure in the chamber 20, and a flap member 46 which is responsive to a flow through the mouthpiece 26 to drive the link 42 and hence actuate the substance supply unit 22 on the development of a predetermined flow rate through the mouthpiece 26, the delivery device provides for actuation of the substance supply unit 22 on either the development of a predetermined actuation pressure in the chamber 20 or a predetermined flow rate through the mouthpiece 26. In this way, the delivery device provides normally for actuation on the development of a predetermined flow rate through the mouthpiece 26, but, where such a flow rate cannot be developed, either by the nasal airway being obstructed or the subject being unable to exhale with sufficient force, actuation is achieved on the development of a predetermined actuation pressure in the chamber 20 of the tubular member 19.

Operation of the delivery device is the same as for the delivery device of the above-described fifth embodiment, but, where a flow rate required for actuation cannot be developed, actuation is achieved on the development of a predetermined actuation pressure in the chamber 20 of the tubular member 19.

Finally, it will be understood that the present invention has been described in its preferred embodiments and can be modified in many different ways without departing from the scope of the invention as defined by the appended claims.

Notably, it will be understood that features of ones of the embodiments can be employed in others of the embodiments. By way of one example, the above-described sixth embodiment could be modified to include the trigger mechanism 30 of the above-described fifth embodiment.

In other embodiments, typically for very expensive and/or potent drugs with potential side-effects, for example, Morphine and Insulin, the above-described devices can be modified to include an electronic controller. This allows even more precise control over the dosing. For particular purposes, it is possible to monitor the concentration of the air escaping from the contralateral nostril of an inert test substance released prior to an active drug to determine and/or optimize the dosing accordingly. Such an electronic controller can also record when the dose was taken and the amount of the delivered dose. It is also envisaged that the above-described devices may also be coupled to a mobile telephone, allowing a subject to be notified when to take the drug and/or if the correct dose has been taken.

It will also be understood that the present invention also finds application in the optimized delivery of substances in liquid or powder form.

It will be further understood that the present invention finds application in multi-dose or single-dose delivery pumps, powder delivery units, pMDIs and nebulizers, with or without a spacer attached.

The invention claimed is:

1. A nasal delivery device for delivering a substance to a nasal cavity of a subject, including:
   a nosepiece for insertion into a nostril of a subject;
   a mouthpiece through which the subject in use exhales;
   a flow path fluidly which connects the nosepiece and the mouthpiece, whereby exhaled air from an exhalation breath is deliverable through the flow path;
   a substance supply unit operable to supply a substance for delivery through the nosepiece; and
   a delivery prevention mechanism configured to prevent exhalation through the flow path, wherein the delivery prevention mechanism comprises first and second members movable relative to one another between first and second configurations, one of the members defining at least a part of the flow path, and the other member including a blocking element which blocks the flow path when the first and second members are in the first configuration and opens the flow path when the first and second members are in the second configuration.

2. The delivery device of claim 1, further including:
   a biasing element for normally biasing the first and second members to the first configuration, whereby a predeterminable biasing force provided by the biasing element has to be overcome in moving the first and second members to the second configuration.

3. The delivery device of claim 1, wherein the substance supply unit includes a dosing unit for supplying at least one substance.

4. The delivery device of claim 3, wherein the dosing unit comprises a nebulizer for supplying an aerosol.

5. The delivery device of claim 3, wherein the dosing unit comprises an aerosol canister for supplying an aerosol.

6. The delivery device of claim 3, wherein the dosing unit comprises a delivery pump unit for supplying an aerosol, a liquid pump unit for supplying a liquid aerosol or a powder pump unit for supplying a powder aerosol.

7. The delivery device of claim 3, wherein the dosing unit comprises a powder delivery unit for delivering a powder aerosol.

* * * * *

UNITED STATES PATENT AND TRADEMARK OFFICE
CERTIFICATE OF CORRECTION

PATENT NO.        : 8,522,778 B2  
APPLICATION NO.   : 12/757626  
DATED             : September 3, 2013  
INVENTOR(S)       : Per Gisle Djupesland Page 1 of 1

It is certified that error appears in the above-identified patent and that said Letters Patent is hereby corrected as shown below:

On the Title Page

Item (56) "Reference Cited", list the reference U.S. Appl. No. 12/955,546, Djupesland.

Signed and Sealed this  
Third Day of December, 2013

Margaret A. Focarino  
*Commissioner for Patents of the United States Patent and Trademark Office*